US006303629B1

(12) United States Patent
Kun

(10) Patent No.: US 6,303,629 B1
(45) Date of Patent: Oct. 16, 2001

(54) METHODS FOR TREATING INFLAMMATION, INFLAMMATORY DISEASES, ARTHRITIS AND STROKE USING PADPRT INHIBITORS

(75) Inventor: Ernestt Kun, Mill Valley, CA (US)

(73) Assignee: Octamer, Inc., Mill Valley, CA (US)

(*) Notice: Subject to any disclaimer, the term of this patent is extended or adjusted under 35 U.S.C. 154(b) by 0 days.

(21) Appl. No.: 09/056,396

(22) Filed: Apr. 6, 1998

Related U.S. Application Data

(63) Continuation-in-part of application No. 08/855,616, filed on May 13, 1997, now Pat. No. 5,908,861.

(51) Int. Cl.[7] .......................... A61K 31/47; A61K 31/35; A61K 31/165

(52) U.S. Cl. ......................... 514/309; 514/456; 514/617; 514/619; 514/622; 514/825

(58) Field of Search .................................. 514/309, 456, 514/617, 619, 622, 825

(56) References Cited

U.S. PATENT DOCUMENTS

| 5,262,564 | 11/1993 | Kun et al. | 562/430 |
|---|---|---|---|
| 5,464,871 | 11/1995 | Kun et al. | 514/617 |
| 5,473,074 | 12/1995 | Kun et al. | 546/141 |
| 5,482,975 | 1/1996 | Kun et al. | 514/619 |
| 5,484,951 | 1/1996 | Kun et al. | 549/285 |
| 5,516,941 | 5/1996 | Kun et al. | 564/166 |
| 5,583,155 | 12/1996 | Kun et al. | 514/457 |

OTHER PUBLICATIONS

Anderson, et al., "Selective Inhibition of Cyclooxygenase (COX)–2 Reverses Inflammation and Expression of COX–2 and Interleukin 6 in Rat Adjuvant Arthritis," *J. Clin. Invest.*—97(11):2672–2679 (1996).

Baeuerle, et al., "Function and Activation of NF–$_k$B in the Immune System," *Ann. Rev. Immunol.*—12:141–179 (1994).

Bauer, et al., "Modification of Growth Related Enzymatic Pathways and Apparent Loss of Tumorigenicity of a ras–Transformed Bovine Endothelial Cell Line by Treatement with 5–Iodo–6–Amino–1,2–Benzopyrone (INH$_2$BP)," *Int. J. Oncol.*—8:239–252 (1996).

Beutler, "TNF, Immunity and Inflammatory Disease: Lessons of the Past Decade," *J. Investigative Medicine*—43(3):227–235 (1995).

Brahn, et al., Animal Models of Rheumatoid Arthritis, *Clin. Orthop. Rel. Res.*—265:52–53 (1991).

Conner, et al., "Suppression of Adjuvant–Induced Arthritis by Selective Inhibition of Inducible Nitric Oxide Synthase," *Eur. J. Pharmacol.*—273:15–24 (1995).

Cowley, et al., "Activation of MAP Kinase Kinase is Necessary and Sufficient for PC12 Differentiation and for Transformation of NIH 3T3 Cells," *Cell*—77:841–852 (1994).

Farrell, et al., "Increased Concentration of Nitrite in Synovial Fluid and Serum Samples Suggest Increased Nitric Oxide Synthesis in Rheumatic Diseases," *Ann. Rhem Dis.*—51:1219–1222 (1992).

Ferrell, "Tripping the Switch Fantastic: How a Protein Kinase Cascade Convert Graded Inputs Into Switch–Like Outputs," *TIBS*—21:460–466 (1996).

Giroir, et al., "Mediators of Septic Shock: New Approaches for Interrupting the Endogenous Inflammatory Cascade," *Critical Car. Med.*—21(5):780–789 (1993).

(List continued on next page.)

*Primary Examiner*—Russell Travers
*Assistant Examiner*—Shengjun Wang
(74) *Attorney, Agent, or Firm*—Albert P. Halluin; Viola T. Kung; Howrey Simon Arnold & White, LLP

(57) ABSTRACT

The present invention is directed to a method for treating inflammation or inflammatory disease, bacterial infection, arthritis and stroke in an animal or mammal, which comprises the steps of administering an effective amount of a pADPRT inhibitory compound to said animal or mammal.

2 Claims, 17 Drawing Sheets

OTHER PUBLICATIONS

Grabowski, et al., "Nitric Oxide Production in Cells Derived from the Human Joint," *Br. J. Rheumatol.*—35:207–212 (1996).

Hauschildt, et al., "Induction of Nitric oxide Synthase in L929 Cells by Tumour–Necrosis Factor α is Prevented by Inhibitors of Poly(ADP–Ribose) Polymerase," *Biochem. J.*—288:255–260 (1992).

Häuselmann, et al., "Nitric Oxide and Proteoglycan Biosynthesis by Human Articular Chondrocytes in Alginate Culture," *FEBS Lett.*—352:361–364 (1994).

Kaur, et al., "Evidence for Nitric Oxide–Medicated oxidative Damage in Chronic Inflammation—Nitrotyrosine in Serum and Synovial Fluid from Rheumatoid Patients," *FEBS Lett.*—350:9–12 (1994).

Kyriakis, et al., "Sounding the Alarm: Protein Kinase Cascades Activated by Stress and Inflammation," *J. Biol. Chem.*—271(40):24313–24316 (1996).

L'Allemain, "Deciphering the Map Kinase Pathway," *Prog. Growth Factor Res.*—5:291–334 (1994).

Levitzki, et al., "Signal–Transduction Therapy—A Novel Approach to Disease Management," *Eur. J. Biochem.*—226:1–13 (1994).

Liles, et al., "Review: Nomenclature and Biologic Significance of Cytokines Involved in Inflammation and the Host Immune Response," *J. Infect Dis.*—172:1573–1580 (1995).

Liu, et al., "Woodchuck Hepatitis Virus Surface Antigen Induces Nitric Oxide Synthesis in Hepatocytes: Possible Role in Hepatocarcinogenesis," *Carcinogenesis*—15(12):2875–2877 (1994).

Lowenstein, et al., "Macrophase Nitric Oxide Synthase Gene: Two Upstream Regions Mediate Induction by Interferon γ and Lipopolysaccharide," *Proc. Natl. Acad. Sci.*—90:9730–9734 (1993).

Marczin, et al., "Tyrosine Kinase Inhibitors Suppress Endotoxin—and IL–1β–Induced NO Synthesis in Aortic Smooth Muscle Cells," *Am. J. Physiol.*—265:H1014–1018 (1993).

Martin, et al., "Role of Interferon Regulatory Factor 1 in Induction of Nitric Oxide Synthase," *J. Exp. Med.*—180:977–984 (1994).

Matsuda, et al., "Signaling Pathways Mediated by the Mitogen–Activated Protein (MAP) Kinase Kinase/MAP Kinase Cascade," *J. Leukocyte Biology*—56:458–553 (1994).

McCartney–Francis, et al., "Suppression of Arthritis by an Inhibitor of Nitric Oxide Synthase," *J. Exp. Med.*—178:749–754 (1993).

Miesel, et al., "Effects of Allopurinol on in vivo Suppression of Arthritis in Mice and ex vivo Modulation of Phagocytic Production of Oxygen Radicals in Whole Human Blood," *Inflammation*—18(6):597–612 (1994).

Muller, et al., "Nuclear Factor Kappa β, a Mediator of Lipopolysaccharide Effects," *Immunobiol.*—187:233–256 (1993).

Murrell, et al., "Nitric Oxide: An Important Articular Free Radical," *J. bone Joint Sur.–Am.*—78:265–274 (1996).

Nathan, "Nitric Oxide as a Secretory Product of Mammalian Cells," *FASEB J.*—6:3051–3064 (1992).

Novogrodsky, et al., "Prevention of Lipopolysaccharide–Induced Lethal Toxicity by Tyrosine Kinase Inhibitors," *Science*—264:1319–1322 (1994).

Ohshima, et al., "Chronic Infections and Inflammatory Processes as Cancer Risk Factors: Possible Role of Nitric Oxide in Carcinogenesis," *Mutation Res.*—305:253–264 (1994).

Oyanagui, "Nitric Oxide and Superoxide Radical are Involved in Both Initiation and Development of Adjuvant Arthritis in Rats," *Life Sci.*—54(17):285–289 (1994).

Pellat–Deceunynck, et al., "Nicotinamide Inhibits Nitric Oxide Synthase mRNA Induction in Activated Macrophages," *Biochem. J.*—297:53–58 (1994).

Sakurai, et al., "Nitric Oxide Production and Inducible Nitric Oxide Synthase Expression in Inflammatory Arthritides," *J. Clin. Invest.*—96:2357–2363 (1995).

Stefanovic–Racic, et al., "Nitric Oxide and Arthritis," *Arthr. Rhemat.*—36(8):1036–1044 (1993).

Stefanovic–Racic, et al., "N–Monomethyl Arginine, an Inhibitor of Nitric oxide Synthase, Suppresses the Development of Adjuvant Arthritis in Rats," *Arthr. Rhemat.*—37:1062–1069 (1994).

Stichtenoth, et al., "Urinary Nitrate Excretion is Increased in Patients with Rheumatoid Arthritis and Reduced by Prednisolone," *Ann Rhem. Dis.*—54:820–824 (1995).

Szabo, et al., "Isoproterenol Regulates Tumour Necrosis Factor, Interleukin–10, Interleukin–6 and Nitric Oxide Production and Protects Against the Development of Vascular Hyporeactivity in Endotoxaemia," *Immunology*—90:950–100 (1997).

Szabo, et al., "DNA Strand Breakage, Activation of Poly-(ADP–Ribose) Synthetase, and Cellular Energy Depletion are Involved in the Cytotoxicity in Macrophases and Smooth Muscle Cells Exposed to Peroxynitrite," *Proc. Natl. Acad.*—93:1753–1758 (1996).

Szabo, et al., "Inhibition by Spermine of the Induction of Nitric Oxide Synthase in J774.2 Macrophages: Requirement of a Serum Factor," *Br. J. Pharmacol.*—112:355–356 (1994).

Ueda, et al., "ADP–Ribosylation," *Ann. Rev. Biochem.*—54:73–100 (1985).

Vane, et al., "New Insights into the Mode of Action of Anti–Inflammatory Drugs," *Inflamm. Res.*—44:1–10 (1995).

Weinberg, et al., "The Role of Nitric Oxide in the Pathogenesis of Spontaneous Murine Autoimmune Disease: Increased Nitric Oxide Production and Nitric Oxide Synthase Expression in MRL–lpr/1pr Mice, and Reduction of Spontaneous Glomerulonephritis and Arthritis by Orally Administered $N^G$–Monomethyl–L–Arginine," *J. Exp. Med.*—179:651–660 (1994).

Whiteman, et al., "Protection Against Peroxynitrite Dependent Tyrosine Nitration and $α_1$–Antiproteinase Inactivation by Some Anti–Inflammatory Drugs and by the Antibiotic Tetracycline," *Ann. Rhem. Dis.*—55:383–387 (1996).

Zingarelli, et al., "Peroxynitrite–Mediated DNA Strand Breakage Activates Poly–Adenosine Diphosphate Ribosyl Synthetase and Causes Cellular Energy Depletion in Macrophages Stimulated with Bacterial Lipopolysaccharide," *J. Immunol.*—156:350–358 (1996).

Erlich, W. et al., "Inhibition of the Induction of Collagenase by Interleukin–1.beta. in Cultured Rabbit Synovial Fibroblasts After Treatment with the Poly(ADP–robise)–polymerase Inhibitor 3–Aminobenzamide," *Chem. Abstr.*, vol. 124, (Columbus, OH USA), Rheumatol. Int. 15(4), 171–172 (1995).

Zhang, J., et al., "Inhibitors of Poly(ADP–ribose) Synthetase for Preventing NMDA Neurotoxicity,", *Chem.Abstr.* vol. 123, Aug. 10, 1995.

CA 124:279169, Kroeger et al., Mar. 1996.*

* cited by examiner

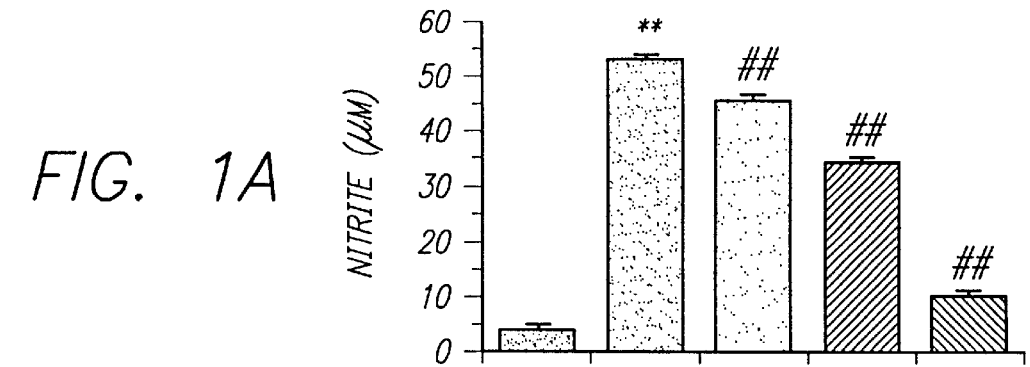
FIG. 1A
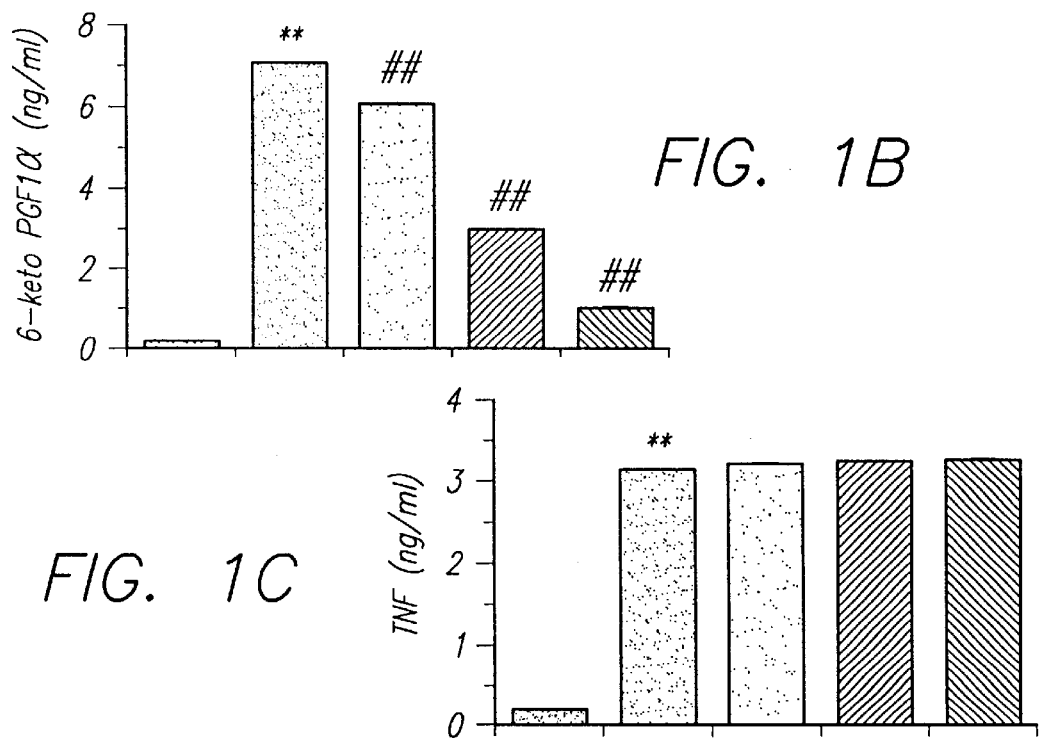
FIG. 1B
FIG. 1C
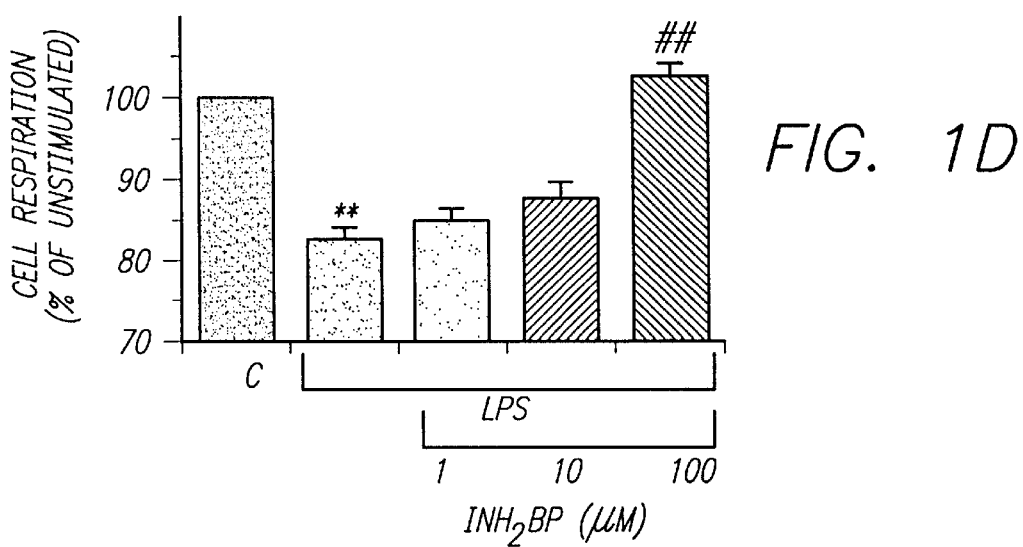
FIG. 1D

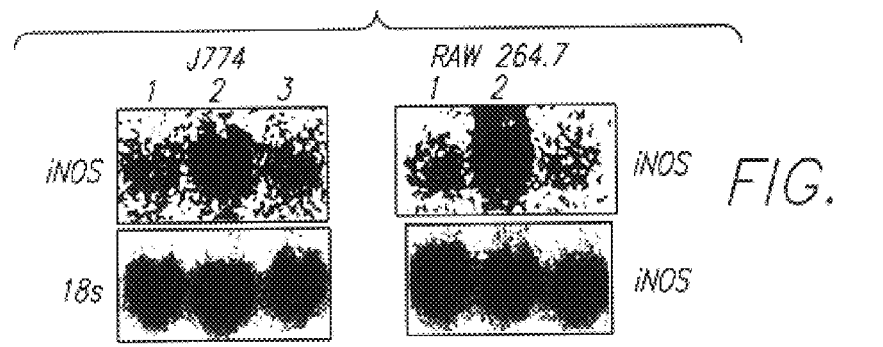
FIG. 2A
FIG. 2B
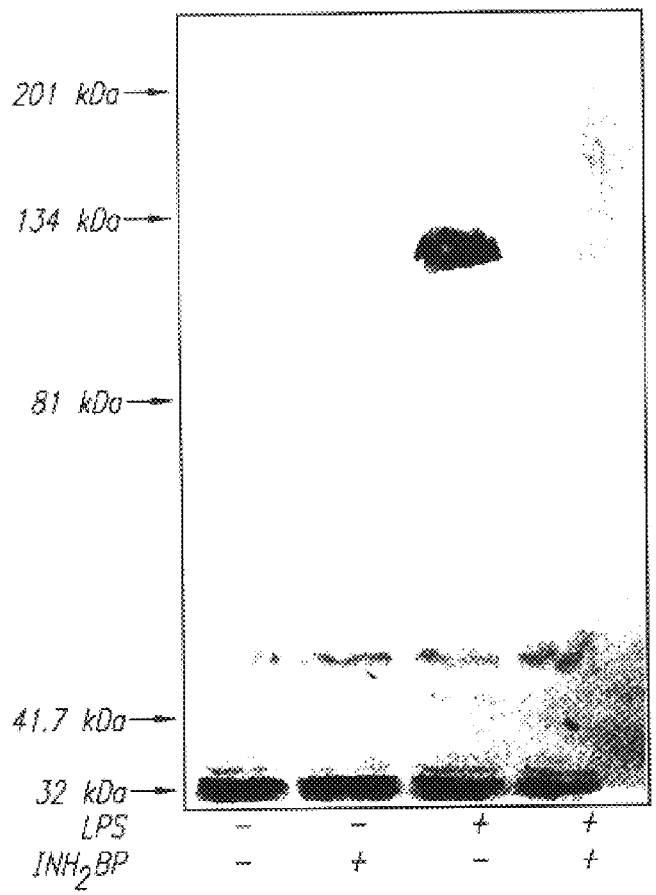
FIG. 2C

METHODS FOR TREATING INFLAMMATION, INFLAMMATORY DISEASES, ARTHRITIS AND STROKE USING PADPRT INHIBITORS

The present application is a continuation-in-part of U.S. Ser. No. 08/855,616 filed on May 13, 1997, now U.S. Pat. No. 5,908,861.

The present invention relates to methods for treating inflammation and inflammatory diseases, arthritis, and stroke in animals. The invention also relates to methods for treating animals having toxicity resulting from infestation by lipopolysaccharides. These methods involve the use of therapeutically effective amounts of pADPRT inhibitory compounds.

BACKGROUND OF THE INVENTION

The use of pADPRT inhibitory compounds have been reported for treating cancer and viral infections. Examples of these methods are described in U.S. Pat. Nos. 5,464,871, 5,473,074; 5,482,975, 5,484,951; 5,516,941, and 5,583,155, the disclosures of which are incorporated herein by reference.

In the published literature, 5-iodo-6-amino-1,2-benzopyrone ($INH_2BP$), a novel inhibitor of the nuclear enzyme poly-ADP ribose polymerase (PADPRT) has recently been shown to inhibit in vivo tumorigenicity in a Ha-ras transfected endothelial cell line (Bauer et al., *Int. J. Oncol.* 8:239–252 (1995) and Bauer et al., *Biochimie* 77:347–377 (1995)). Treatment with $INH_2BP$ has also resulted in changes in topoisomerase I and II and MAP kinase activity Based on the effects observed, a hypothesis regarding the potential use of $INH_2BP$ in the therapy of cancer has been put forward.

Malignant growth and inflammatory processes may feature the activation of certain common cellular signal transduction pathways, e.g., MAP kinase (Kyriakis et al., *J. Biol. Chem.* 271:24313–24316 (1996) and Ferrell, *TIBS* 21:460–466 (1996)). Chronic inflammation frequently leads to carcinogenic transformation, as demonstrated, for example, in the case of the intestine. In our study, the production of multiple proinflammatory mediators was induced by bacterial lipopolysaccharide (endotoxin, LPS). LPS is known to induce a multitude of cellular reactions and triggers a systemic inflammatory response. LPS-induced pro-inflammatory mediators include tumor necrosis factor alpha (TNF), interleukin-1, interferon-gamma, whereas anti-inflammatory mediators include interleukin-10 (IL-10) and interleukin-13 (Deltenre et al., *Acta Gastroenterol Belg.* 58:193–200 (1995), Beutler, *J. Invest. Med.* 42:227–35 (1995), Liles et al., *J. Infect Dis.* 172:1573–80 (1995), and Giroir, *Critical Car. Med.* 21:780–9 (1993)). As a consequence of the production of these inflammatory cytokines, LPS initiates the production of inflammatory free radicals (oxygen-centered, such as superoxide, and nitrogen-centered radicals, such as nitric oxide (NO) and of prostaglandins (Nathan, *FASEB J.* 6:3051–3064 (1992), Vane, *Proc. Roy. Soc. Lond B* 343:225–246 (1993), and Szabo, *New Horizons* 3:3–32 (1995)). The production of NO in inflammation is due to the expression of a distinct isoform of NO synthase (iNOS), while the production of inflammatory cytokines is explained by the expression of a distinct isoform of cyclooxygenase (cyclooxygenase-2, COX-2), iNOS, COX-2, as well as other pro-inflammatory cytokines and free radicals which play an important role in the LPS-induced inflammatory response. Moreover, NO (or its toxic byproduct, peroxynitrite), has been implicated as a key mediator leading to the transformation of the inflammatory response into a carcinogenic process (Bartsch et al., *Pharmacogenetics* 2:272–7 (1994), Liu et al., *Carcinogenesis* 15:2875–7 (1992) and Ohshima et al., *Mutation Res.* 305:253–64 (1994)).

There are a multitude of intracellular processes which precede the production of proinflammatory mediators. Activation of tyrosine kinases (Levitzki, A., *Eur. J. Biochem.* 226:1–13 (1994), Novogrodsky et al., *Science* 264:1319–22 (1994), Marczin et al., *Am. J. Physiol.* 265:H1014–1018 (1993)), mitogen-activated protein kinase (MAP kinase, Matsuda et al., *J. Leukocyte Biol.* 56:548–53 (1994), L'Allemain, *Progr. Growth Factor Res.* 5:291–334 (1994), and Cowley et al., *Cells* 77:841–52 (1994)); and the nuclear factor kappa B (NF-kB) pathway (Baeuerle et al., *Ann. Rev. Immunol.* 12:141–79 (1994), Schreck et al., *Free Radical Res. Comm.* 17:221–37 (1992) and Muller et al., *Immunobiol.* 187:233–56 (1993)) are recognized as important factors in the inflammatory response and contribute to the expression or production of inflammatory mediators.

SUMMARY OF THE INVENTION

One aspect of the invention is a method for treating inflammation or inflammatory disease in an animal or mammal, which comprises the steps of administering an effective amount of a pADPRT inhibitory compound.

Another aspect of the invention is a method for treating inflammation or inflammatory disease in an animal or mammal, which comprises the steps of administering an effective amount of a pADPRT inhibitory compound wherein the pADPRT inhibitory compound is selected from the group consisting of:

a compound having the formula:

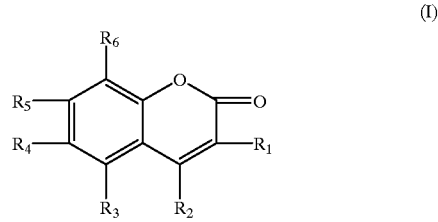

(I)

wherein $R_1$, $R_2$, $R_3$, $R_4$, $R_5$, and $R_6$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, $R_5$, and $R_6$ is selected from the group consisting of amino, nitroso or nitro; a compound having the formula:

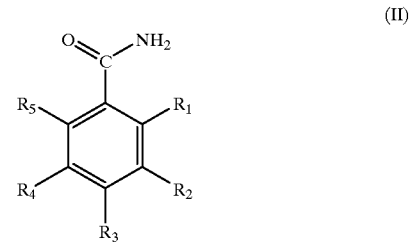

(II)

wherein $R_1$, $R_2$, $R_3$, $R_4$, and $R_5$ are each selected from the group consisting of hydrogen, hydroxy, amino, alkyl, alkoxy, cycloalkyl or phenol, optionally substituted with alkyl, alkoxy, hydroxy or halo, and only one of R$_1$, R$_2$, R$_3$, R$_4$, and R$_5$ is selected from the group consisting of amino, nitroso or nitro; and a compound having the formula:

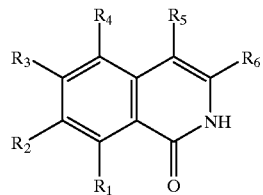

(III)

wherein R$_1$, R$_2$, R$_3$, R$_4$, and R$_5$ are each selected from the group consisting of hydrogen, hydroxy, amino, alkyl, alkoxy, cycloalkyl or phenol, optionally substituted with alkyl, alkoxy, hydroxy or halo, and only one of R$_1$, R$_2$, R$_3$, R$_4$, and R$_5$ is amino. Preferred pADPRT compounds include: 6-amino-1,2-benzopyrone, 3-nitrosobenzamide, 5-amino-1(2H)-isoquinolinone, 7-amino-1(2H)-isoquinolinone, and 8-amino-1(2H)-isoquinolinone. Particularly preferred is the compound 5-iodo-6-amino-1,2-benzopyrone.

Still another aspect of the invention is a method of treating arthritis in an animal comprising the step of administering an effective amount of or a pADPRT inhibitory compound wherein the compound has the structural formula noted above as compounds I, II or III. Especially preferred is the compound 5-iodo-6-amino-1,2-benzopyrone.

Still another aspect of the invention is a method of treating cerebrovascular accidents such as stroke in an animal comprising the step of administering an effective amount of or a pADPRT inhibitory compound wherein the compound has the structural formula noted above as compounds I, II or III. Especially preferred is the compound 5-iodo-6-amino-1,2-benzopyrone.

The pADPRT inhibitory compounds of the invention may be prepared by the methods described in U.S. Pat. Nos. 5,464,871, 5,473,074; 5,482,975, 5,484,951, 5,516,941, and 5,583,155, the disclosures of which are incorporated herein by reference.

The preferred compounds for use in the methods of the invention include those where the halo group is iodo, and one of the R groups is amino. Also, it has been found that the pADPRT inhibitory activity is strongly exhibited when an iodo moiety is adjacent to an amino moiety. In any event, the compounds to be used in the methods of the invention should have pADPRT inhibitory activity. The compounds may be used as is, or preferably in combination with a pharmaceutically acceptable acid addition salt or other suitable pharmaceutical carrier known in the art.

Those of skill in the art will readily understand that the pathologies and disease states expressly stated herein are not intended to be limiting. Rather, the compounds of the present invention may be used to treat any disease which features an inflammatory response. That is, the compounds of the present invention have pADPRT inhibitory activity and may be effectively administered to ameliorate any disease state which is mediated all or in part by pADPRT.

BRIEF DESCRIPTION OF THE DRAWINGS

FIG. 1 describes the effect of INH$_2$BP on the development of carrageenan-induced paw edema. Data show paw volumes at 1–4 h after carrageenan injection (means ±S.E.M., n=6 animals in each group). There was a significant increase in the paw volume from hour 1 (p<0.01), and there was a significant inhibition of the development of paw edema of INH$_2$BP at 1–4 hours (**p<0.02).

FIG. 2 describes the effect of INH$_2$BP on the onset of collagen-induced arthritis. The percentage of arthritic mice (mice showing clinical scores of arthritis >1) are represented. The arrow at 21 days represents the time of the second collagen immunization, the horizontal bar from day 25 represents the time of the start of treatment with INH$_2$BP (N=6) or VEHICLE (N-10).

DESCRIPTION OF THE PREFERRED EMBODIMENTS OF THE INVENTION

Definitions as used Herein

Figure 3A:
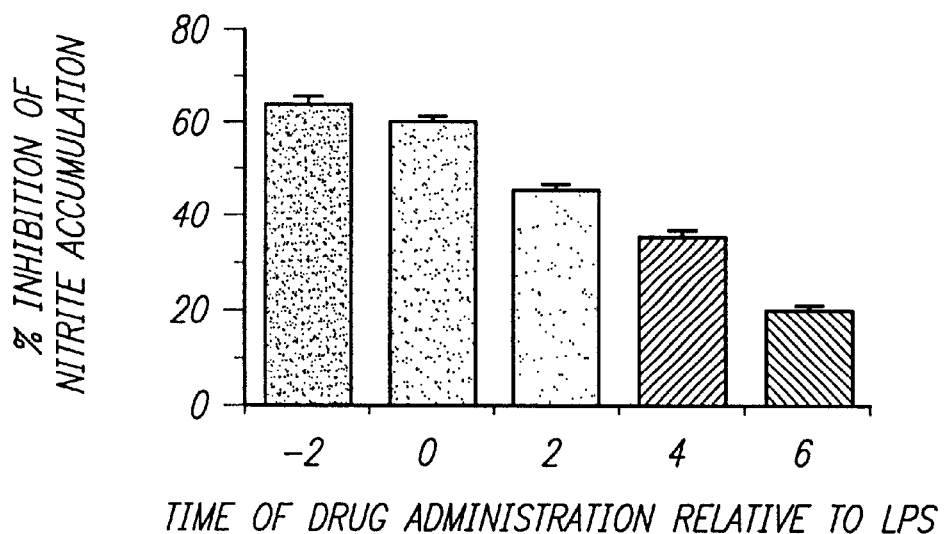
FIG. 3 describes the effect of INH$_2$BP on the severity of collagen-induced arthritis. The median arthritic score during collagen-induced arthritis is represented. The arrow at 21 days represents the time of the second collagen immunization, the horizontal bar from day 25 represents the time of the start of treatment with INH$_2$BP (n-6) or vehicle (n=10). There was a significant increase in the arthritic score from day 26 (Ip<0.01), and there was a significant suppression of the arthritic score by INH$_2$BP between days 26–35 (#p<0.05).

"Inflammatory" diseases refers to diseases or conditions where there is an inflammation of the body tissue. Such diseases include for example, Chron's disease, Barrett's disease, arthritis, multiple sclerosis, cardiomyopathic disease, colitis, infectious meningitis, encephalitis, and the like. "ADPRT" refers to adenosinediphosphoribose transferase and is also known as poly(ADP-ribose) polymerase (EC 2.4.99), a specific DNA-binding nuclear protein of eucaryotes that catalyzes the polymerization of ADP-ribose. The enzymatic process is dependent on DNA. The term is synonymous with the term "PARS" or poly (ADP-ribose) synthetase in the literature. That is, the terms are used interchageably herein and in the literature as is readily appreciated by those skilled in the art.

"Alkyl" refers to saturated or unsaturated branched or straight chain hydrocarbon radical. Typical alkyl groups include methyl, ethyl, propyl, isopropyl, butyl, isobutyl, tertiary butyl, pentyl, hexyl and the like.

"Alkoxy" refers to the radical —O-alkyl. Typical alkoxy radicals are methoxy, ethoxy, propoxy, butoxy and pentoxy and the like.

"Arthritis" refers to any condition affecting the joints of the skeletal system including degenerative conditions and autoimmune conditions. Such conditions may generally be characterized by an influx of inflammatory cells.

"Cycloalkyl" refers to saturated monocyclic hydrocarbon radical containing 3–8 carbon atoms such as cyclopropyl, cyclobutyl, cyclopentyl, cyclohexyl, cycloheptyl, cyclooctyl, and the like.

"Substituted phenyl" refers to all possible isomeric phenyl radicals such as mono or disubstituted with a substituent selected from the group consisting of alkyl, alkoxy, hydroxy, or halo.

The pADPRT inhibitory compounds of the invention (notably compounds defined above as compounds I, II or III) are potent, specific and non-toxic anti-inflammatory compounds, that can be used for conditions and diseases typically known for inflammation, such as arthritis, Chron's disease, Barrett's disease, and the like. Also, these compounds are useful in the treatment of conditions associated with endotoxin poisoning, especially those associated with gram negative bacteria infections. Moreover, the compounds are useful for treating arthritis and stroke. The preferred compounds of the present invention such as 5-iodo-6-amino-1,2-benzopyrone are especially useful in that they have very low, if any, toxicity.

In practice, the compounds of the invention, or their pharmaceutically acceptable salts, may be administered in amounts that are sufficient to inhibit inflammatory conditions or disease and/or prevent the development of inflammation or inflammatory disease and may be used in the pharmaceutical form most suitable for such purposes. Likewise, the compounds of the invention may be administered in amounts which will be sufficient to inhibit arthritis and pathology that is a sequelae of cerebrovascular accident.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is oral. However, in some instances it may be necessary to administer the composition in parenteral form.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of one or more active pADPRT inhibitory compounds or possibly the pharmaceutically acceptable salts thereof. In addition, it may include any conventional pharmaceutical excipients and other medicinal or pharmaceutical drugs or agents, carriers, adjuvants, diluents, etc., as customary in the pharmaceutical sciences.

For solid compositions such excipients may include pharmaceutical grades of mannitol, lactose, starch, magnesium stearate, sodium saccharin, talcum, cellulose, glucose, sucrose, magnesium carbonate, and the like may be used. The active pADPRT inhibitory compound defined above may be also formulated as suppositories using, for example, polyalkylene glycols, for example, propylene glycol, as the carrier.

Liquid, particularly injectable compositions can, for example, be prepared by dissolving, dispersing, etc. the active compound in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and other substances such as, for example, sodium acetate, triethanolamine oleate, etc.

Also, if desired, the pharmaceutical composition to be administered may contain liposomal formulations comprising a phospholipid, a negatively charged phopholipid and a compound selected from cholesterol, a fatty acid ester of cholesterol or an unsaturated fatty acid.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of slow-release or sustained-released systems, which assures that a constant level of dosage is maintained, according to U.S. Pat. No. 3,710,795, the disclosure of which is incorporated herein by reference.

Any of the above pharmaceutical compositions may contain 0.1–99%, preferably 1–70% of the active pADPRT inhibitory compounds, especially the halo-C-amino, nitroso or nitro compounds of the formulae I, II or III, above as active ingredients.

The compounds of the present invention including 5-iodo-6-amino-1,2-benzopyrone ($INH_2BP$) have been shown to regulate a variety of cellular signal transduction pathways and to abrogate in vivo tumorigenicity by a Ha-ras transfected endothelial cell line. As one aspect of the present invention demonstrates the effect of pADPRT inhibitory compounds such as $INH_2BP$ on the activation by endotoxin (bacterial lipopolysaccharide, LPS) on the production of the inflammatory mediators tumor necrosis factor alpha (TNF), interleukin-10 (IL-10) and interleukin-6 (IL-6), nitric oxide (NO) and prostaglandins in vitro and in vivo. In addition, the pADPRT inhibitory effects of the compounds of the present invention such as $INH_2BP$ on the activation of mitogen-activated protein kinase (MAP kinase) and nuclear factor kB (NF-kB) in vitro.

In cultured J774 and RAW 264.7 macrophages, LPS induced the production of prostaglandin metabolites, the release of TNF and the expression of the inducible isoform of NO synthase (iNOS). The production of prostaglandins and of NO are inhibited by $INH_2BP$ in a dose-dependent manner, while the short-term release of TNF-alpha is unaffected. $INH_2BP$ markedly suppresses LPS-mediated luciferase activity in RAW cells transiently transfected with a full length (−1592 bp) murine macrophage iNOS promoter-luciferase construct, but not in a deletional construct consisting of −367 bp. In vivo, $INH_2BP$ pretreatment inhibits the induction of iNOS by LPS in rats, does not affect the LPS-induced TNF and IL-6 response, but enhances LPS-induced IL-10 production. $INH_2BP$ pretreatment markedly improves the survival of mice in a lethal model of endotoxin shock. These results demonstrate that pADPRT inhibitory compounds such as $INH_2BP$ have potent anti-inflammatory action in vitro and in vivo.

The following examples serve to illustrate the invention. They should not be construed as narrowing it, or limiting its scope.

EXAMPLE 1

Cell Culture.

The mouse macrophage cell lines J774 and RAW 264.7 were cultured in Dulbecco's modified Eagle's medium (DMEM) as described (Szabo et al., *Proc. Natl. Acad. Sci. U.S.A.* 93:1753–1758 (1996) and Zingarelli et al., *J. Immunol.* 156:350–358 (1996)). In separate studies, peritoneal macrophages were obtained from male Wistar rats and cultured in vitro for 24 hours in the absence or presence of LPS and with or without $INH_2BP$. Rats were sacrificed and peritoneal macrophages taken and cultured in DMEM. Cells were treated with *E. Coli* LPS (10 mg/ml) or LPS and INF (50 u/ML) for various times, in the presence or absence of various concentrations (1–150 mM) $INH_2BP$ or other pharmacological inhibitors.

MAP kinase related assays.

Raw cells were washed in PBS and collected and lysed using 100 ml of lysis buffer per million cells. (50 mM Tris-HCl pH 7.4, 1% NP-40, 0.4 M NaCl, 0.1 mM $NaVO_3$, 50 mM KF, 1 mM EGTA, 2 mM PMSF, 25 nM okadaic acid, 1 mg/mL of each leupeptin, aprotinine, arnastatine and antipaine). Lysis was carried out for 20 minutes on ice followed by a 14 min. centrifugation at 13000 rpm in an Eppendorf centrifuge. Supernatants were saved and their protein content was assayed using the Bio-Rad dye assay.

In gel MAP kinase assay.

Protein samples (50 mg/lane) were electrophoresed in a 10% SDS-PAGE gel containing immobilized myelin basic protein (MBP, 250 mg/mL gel). After electrophoresis, the gel was washed once with 50 mM TRIS-HCl pH 7.7 buffer (25 mL, 20 min.), followed by two 30 min. incubations with the same buffer containing 25% i-propanol. The gel was then washed once with the Tris-HCl buffer and soaked into a solution of 50 mM Tris-HCl pH 7.7, 7 mM 2-mercaptoethanol, 5 M guanidine hydrochloride (50 mL) for an hour, changing the incubating solution at 30 minutes. The proteins were then renatured by incubating the gel in five changes of a solution of 50 mM TRIS-HCl pH 7.7, 7 mM 2-mercaptoethanol, 0.04% NP-40 over a 16 hour period of time. The gel was then washed twice and pre-incubated for half an hour in a solution containing 50 mM TRIS-HCl pH 7.7, 5 mM $MgCl_2$, 7 mM 2-mercaptoethanol. The final incubation was carried out in the same solution supplemented with 10 mM of [$^{32}$P]-dATP (50 mCi/assay) for an hour. At the end of the incubation, the gel was washed free of unbound radioactivity using 3×25 mL of 10% TCA and 3×25 mL of 10% acetic acid, dried and auto-radiographed (Sasaki et al., *Biochem. J.* 311:829–34 (1995)).

MAP kinase Western blotting.

One hundred mg of cell extract proteins were loaded onto a 10% SDS-PAGE gel, electrophoresed, transblotted onto nitrocellulose membrane and immunoprobed. The first antibody (anti-MAP kinase) was from UBI, the second antibody was alkaline phosphatase labeled and from NEN Biolabs. Detection was by enhanced chemiluminesence (Bauer et al., *Int. J. Oncol.* 8:239–252 (1995)).

Preparation of nuclear extracts and NF-kB Western blotting.

Cells were treated with LPS in the presence and absence of $INH_2BP$ for 90 minutes. Mininuclear extracts were prepared as described (Hassanain et al., *Anal. Biochem.* 213:162–7 (1993)). Briefly, cells were scraped, briefly centrifuged and pellets resuspended in 400 ml cold Buffer A (Hepes pH 7.9 (10 mM), KCl (10 mM), EDTA (0.1 mM), EGTA (0.1 mM), DTT (1 mM), PMSF (0.5 mM), pepstatin A (1 mg/ml), leupeptin (10 mg/ml), and aprotinin (10 mg/ml)), on ice for 15 minutes, in the presence of 25 ml 1% NP-40. Then, samples were vortexed, centrifuged for 1 minute at 10,000 g, and the pellet resuspended with 100 ml Buffer B (Hepes pH 7.9 (20 mM), NaCl (400 mM), EDTA (1 mM), EGTA (1 mM), DTT (1 mM), PMSF (0.5 mM), pepstatin A (mg/ml), leupeptin (10 mg/ml) and aprotinin (10 mg/ml)). After shaking on a rocker platform for 15 minutes at 4° C., samples were centrifuged for 15 minutes at 100,000 g at 4° C. 70 ml aliquots were then treated with 150 ml SDS-PAGE sample buffer. Western blotting was performed as described above, with rabbit anti-mouse NF-kB primary antibody (Santa Cruz Biotechnology, Santa Cruz, Calif.) 1:750 in Tween TBS (0.02%).

Measurement of nitrite or nitrite/nitrate concentration.

Nitrite in culture supernatants at 24 hours after stimulation was measured as described by Szabo et al., *Proc. Natl. Acad. Sci. U.S.A.* 93:1753–1758 (1996); Zingarelli et al., *J. Immunol.* 156:350–358 (1996); and Szabo et al., *Br. J. Pharmacol.* 112:355–356 (1994) by adding 100 ml of Griess reagent (1% sulfanilamide and 0.1% naphthylethylenediamide in 5% phosphoric acid) to 100 ml samples of medium. The optical density at 550 nm ($OD_{550}$) was measured using a Spectramax 250 microplate reader (Molecular Devices, Sunnyvale, Calif.). For the determination of total nitrite/nitrate concentrations in plasma samples, nitrate was reduced to nitrite by incubation with nitrate reductase (Zingarelli et al., supra).

Measurement of 6-keto prostaglandin $F_{1a}$.

6-keto prostaglandin $F_{1a}$ production at 4 hours after LPS stimulation was measured in 100 ml samples of cell culture supernatant using a specific radioimmunoassay (Szabo et al., *Br. J. Pharmacol.* 112:355–356 (1994)).

Cytokine measurements.

Cytokine levels in plasma and cell culture supernatants were determined by ELISA. Plasma levels of IL-10 and IL-6 were measured using ELISA kits from Endogen (Endogen Inc., Boston, Mass.). Concentrations of TNF-a in the plasma and cell culture supernatants were determined using ELISA kits from Genzyme (Genzyme Corp., Boston, Mass.) as described (Szabo et al., *Immunology* 90:95–100 (1997)).

Measurement of mitochondrial respiration.

Mitochondrial respiration at 24 hours was assessed by the mitochondrial-dependent reduction of 3-(4,5-dimethylthiazol-2-yl)-2,5-diphenyltetrazolium bromide to formazan (Szabo et al., *Proc. Natl. Acad. Sci. U.S.A.* 93:1753–1758 (1996) and Zingarelli et al., supra).

Northern blotting for iNOS mRNA.

After exposing cells to LPS in the presence or absence of $INH_2BP$ for 4 hours, total RNA was extracted as described using TRIZOL. Aliquots containing 15 mg total RNA underwent electrophoresis on a 1% agarose gel containing 3% formaldehyde. RNAs were blot transferred to nylon membrane and UV auto-crosslinked. Membranes were hybridized as described by Lowenstein et al., *Proc. Natl. Acad. Sci. U.S.A.* 90:9730–9734 (1993) overnight at 42° C. with a murine iNOS cDNA probe ($10^6$ cpm/mL) labeled with [$^{32}$P]-dCTP (specific activity, 3,000 Ci/mM; NEN) by random priming (Pharmacia, Piscataway, N.J.). The hybridized filters were serially washed at 53° C. using 2× sodium citrate, sodium chloride, 0.1% SDS and 25 mM $NaHPO_4$, 1 mM EDTA, 0.1% SDS solutions. After probing for iNOS, membranes were stripped with boiling 5 mM EDTA and rehybridized with a [$^{32}$P]-radiolabeled ologonucleotide probe for 18S ribosomal RNA as a housekeeping gene. After washing, exposure was carried out overnight using a Phosphor Imager screen.

iNOS Western blotting.

Cells were treated with LPS in the presence and absence of pADPRT inhibitor for 20 hours. Cells were then scraped in cold PBS and centrifuged at 14,000 g for 30 seconds. The supernatant was removed and lysis buffer containing RIPA (500 mL), aprotin (10 mg/ml), and PMSF (0.5 mM) was added. DNA was sheered by passing samples through a 22 gauge needle. Protein content was determined by the Bradford method (BIO-Rad). Cytosolic protein (200 mg/lane) was added to SDS-PAGE buffer, boiled for 5 minutes, separated with 7.5% SDS-PAGE, and transferred to nitrocellulose membranes (0.2 mm) using a Semi-Dry method with an isotachophoretic buffer system. After 1 hour blocking in 3% gelatin and subsequent washing, the samples were immunoblotted in Tween Tris Buffered Saline (TTBS) and 1% gelatin, with primary rabbit anti-mouse iNOS (upstate Biotechnology, Lake Placid, N.Y.) 1:1000 in TTBS (0.0%) for 2.5 hours. An alkaline phosphatase-conjugated goat anti-rabbit iGG antibody was used as secondary antibody. Antibody binding was visualized by nitrobule tetrazolium/5-bromo-4-chloro indolyl phosphate (NBT/BCIP) in carbonate buffer (BIO-RAD).

Measurement of iNOS activity.

Cells were treated with LPS in the presence and absence of a pADPRT inhibitor for 12 hours. The measurement of the calcium-independent conversion of L-arginine to L-citrulline in homogenates of the J774 cells or in lung homogenates was used as an indicator of iNOS activity as described (Szabo et al., *Br. J. Pharmacol.* 112:355–356 (1994)). Cells were scraped or lungs were put into a homogenation buffer composed of 50 mM Tris HCl, 0.1 mM EDTA, 0.1 mM EGTA and 1 mM phenylmethylsulfonyl fluoride (pH 7.4) and homogenized in the buffer on ice using a Tissue Tearor 985-370 homogenizer (Biospec Products, Racine, Wis.). Conversion of [$^3$H]-L-arginine to [$^3$H]-L-citrulline was then measured in the homogenates. Homogenates (30 ml) were incubated in the presence of [$^3$H]-L-arginine (10 mM, 5 kBq/tube), NADPH (1 mM), calmodulin (30 nM), tetrahydrobiopterin (5 mM) and EGTA (5 mM) for 20 minutes at 22° C. Reactions were stopped by dilution with 0.5 ml of ice cold HEPES buffer (pH 5.5) containing EGTA (2 mM) and EDTA (2 mM). Reaction mixtures were applied to Dowex 50W (Na+ form) columns and the eluted [$^3$H]-L-citrulline activity was measured by scintillation counting.

Functional assay of iNOS promoter.

J774 cells were resistant to our attempts to transiently transfect them using the 25 calcium phosphate, lipofectin, and lipofectamin methods, transfection studies were performed in RAW 264.7 cells. iNOS promoter activity was evaluated by transient transfection of RAW 264.7 cells with reporter gene constructs incorporating the 5' murine macrophage iNOS promoter region upstream from the reporter gene luciferase kindly provided by Dr. Charles J. Lowenstein, Johns Hopkins University (Lowenstein et al., *Proc. Natl. Acad. Sci. U.S.A.* 90:9730–9734 (1993)). Two constructs were used: a full length promoter construct (−1592 bp) and a deletional construct consisting of −367 bp. Cells were plated into 6-well culture plates at approximately 50% confluence and transfected with the respective iNOS promoter-luciferase construct in equimolar amounts using cationic liposomes (Lipofectin, Gibco). In order to control for differences in transfection efficiencies, cells were co-transfected with pSV40-β-galactosidase. After transfection, cells were allowed to recover overnight, then subsequently treated with media alone (control), LPS (10 mg/ml), or LPS plus INH$_2$BP (100 mM). After 4 hours of treatment, cells were washed once in PBS, lysed in reporter lysis buffer (Promega), and analyzed for luciferase activity.

In vivo experiments.

Male Wistar rats and Male BALB/c mice were obtained from Charles River Laboratories (Wilmington, Mass. or Budapest, Hungary). Animals received food and water ad libitum, and lighting was maintained on 12 hour cycle. Rats were injected i.p. with *E. coli* LPS (15 mg/kg) and sacrificed at 6 hours. Plasma samples were taken for nitrite/nitrate determinations and lung samples for iNOS measurements. Separate groups of rats were treated with INH$_2$BP (10 mg/kg i.p.) 10 minutes prior to LPS or 2 hours after LPS injection.

In studies for the measurement of LPS-induced cytokine response, mice were injected i.p. with either drug vehicle, or with INH$_2$BP (10 mg/kg) in a volume of 0.1 ml/10 g body weight. Half an hour later they were challenged with 4 mg/kg of i.p. LPS. The animals were killed at 90 minutes after LPS treatment, blood was collected in ice-cold Eppendorf tubes containing EDTA, and centrifuged for 10 minutes at 4° C. The plasma was stored at −7° C. until assayed.

In survival studies with mice, animals were subjected to i.p. injection of LPS (120 mg/kg) at time 0, and survival was monitored for 42 hours after LPS. Separate groups of mice received vehicle or INH$_2$BP treatment (0.1–10 mg/kg i.p.) at times −18 hours, −4 hours, 0 hours, 6 hours, 24 hours and 30 hours relative to LPS.

Materials.

DMEM, RPM1, TRIZOL and fetal calf serum were from Gibco (Grand Island, N.Y.). [$^3$H]-NAD$^+$ and [$^{32}$P]-NAD$^+$ were obtained from DuPont NEN (Boston, Mass.). Alcohol dehydrogenase and ND$^+$ were obtained from Boehringer Mannheim (Indianapolis, Ind.). PD 98059 was obtained from Cal Biochem (La Jolla, Calif.). All other drugs were obtained from Sigma (St. Louis, Mo.).

Statistical evaluation.

All values in the figures and text are expressed as mean ±standard error of the mean (S.E.M.) of n observations (n≧4). Student's unpaired t-test was used to compare means between groups. A p-value less than 0.05 was considered statistically significant.

Results

Figure 3B:
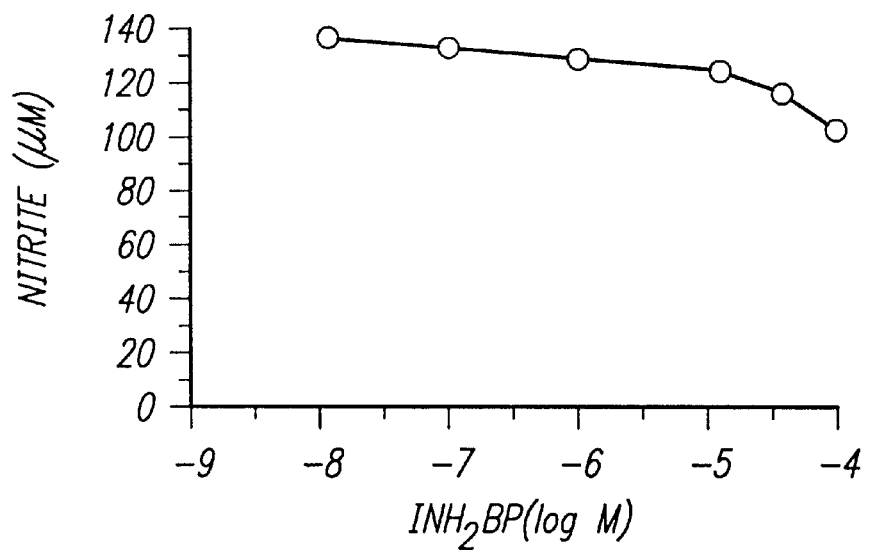

INH$_2$BP suppresses LPS-induced nitric oxide and prostaglandin but not TNF-α production in J774 macrophages INH$_2$BP treatment caused a dose-dependent inhibition of LPS-induced nitrite formation in J774 macrophages (FIG. 1*a*). Similarly, INH$_2$BP suppressed LPS-induced production of 6-keto prostaglandin F$_{1a}$ (FIG. 1*b*), but not the production of TNF (FIG. 1*c*), and restored the LPS-induced suppression of mitochondrial respiration (FIG. 1*d*). INH$_2$BP caused a marked inhibition of iNOS mRNA and protein expression (FIGS. 2*a–c*). The inhibition of nitrite production by INH$_2$BP was greatly diminished when the agent was given several hours LPS, as opposed to prior to the stimulus of iNOS induction (FIG. 3*a*). Moreover, the inhibitory effect of INH$_2$BP on iNOS was greatly reduced when LPS was used in combination was with interferon-gamma (INF-g 50 u/mL) for immunostimulation (FIG. 3*b*).

Selective regulation of the induction of the iNOS promoter by INH$_2$BP

Figure 4:
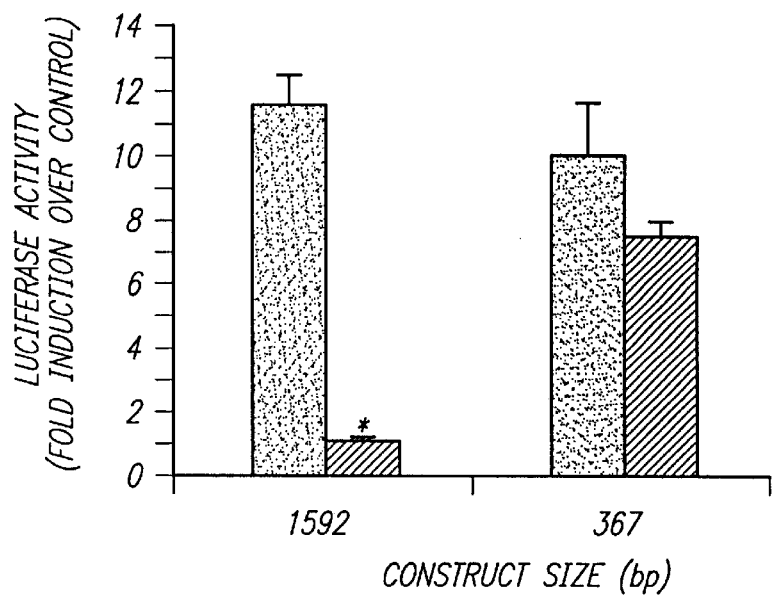
FIG. 4 describes the representative histology of paw (a) control; (b) arthritic; (c) INH$_2$BP treatment+arthritis. Magnification: ×20.

In order to further study the regulation of iNOS promoter by INH$_2$BP we performed transient assays using murine macrophage iNOS promoter-luciferase constructs. Consistent with previous data (Lowenstein et al., supra), we found an important role for LPS-mediated transcriptional regulation of murine macrophage iNOS, as evidenced by a 10 to 12-fold induction of luciferase activity by LPS (FIG. 4). Co-treatment of cells transfected with the full length (−1592 bp) promoter construct with INH$_2$BP, completely inhibited LPS-mediated luciferase activity (FIG. 4). However, similar co-treatment of cells transfected with the −367 bp deletional construct did not significantly affect LPS-mediated luciferase activity (FIG. 4).

In vivo antiinflammatory effects of INH$_2$BP

Figure 5A:
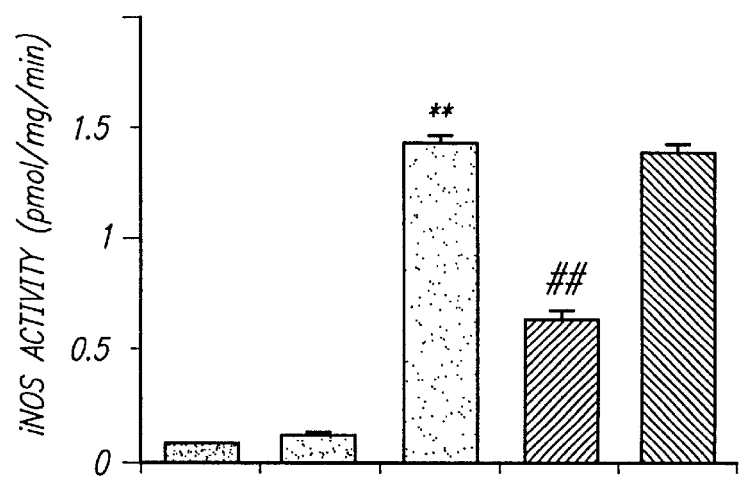
FIG. 5 represents the suppression of the induction of iNOS in conscious rats treated with INH$_2$BP. iNOS activity in lung homogenates (a) and plasma nitrite-nitrate concentrations (b) in control rats (c), in rats injected with INH$_2$BP (INH$_2$BP); in rats injected with LPS (15 mg/kg i.p. for 6 h); and the effect of treatment with INH$_2$BP (10 mg/kg i.p.), when given 10 min. prior to LPS (INH$_2$BP+LPS) or at 2 hours after LPS (LPS+INH$_2$BP). ** represents a significant effect of LPS when compared to controls (p<0.01); ## represents significant inhibition by the pADPRT inhibitor (p<0.01); n=4–5.
Figure 5B:
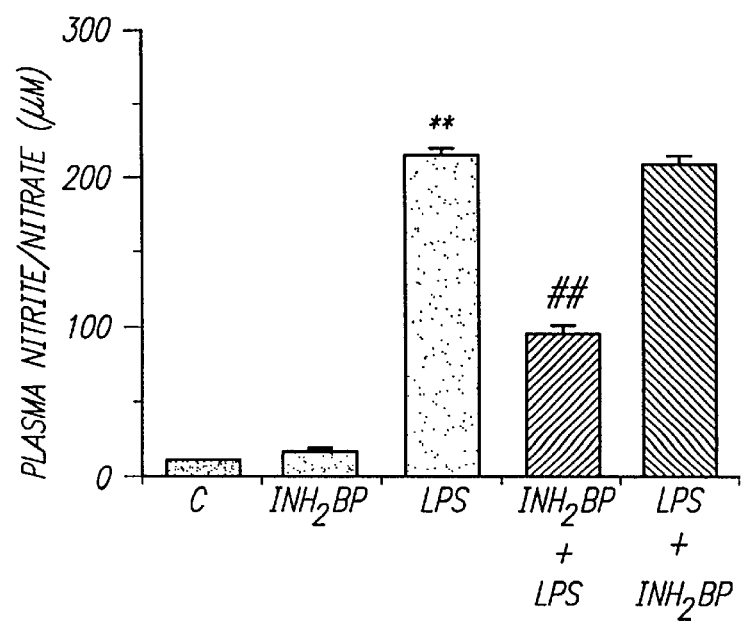

INH$_2$BP pretreatment significantly reduced the LPS-induced increase in plasma nitrite-nitrate and the increase in pulmonary iNOS activity in conscious rats (FIG. 5). The inhibitory effect of INH$_2$BP on NO production was reduced when the agent was added to the cells or to the animals several hours after LPS stimulation (FIG. 5). Similarly to the transformed cell lines, treatment with 100 mM INH$_2$BP significantly reduced (by 56±7%, p<0.01) nitrite production in primary cells (peritoneal macrophages obtained from rats) stimulated with LPS (10 mg/ml) in vitro (n=4).

Figure 6A:
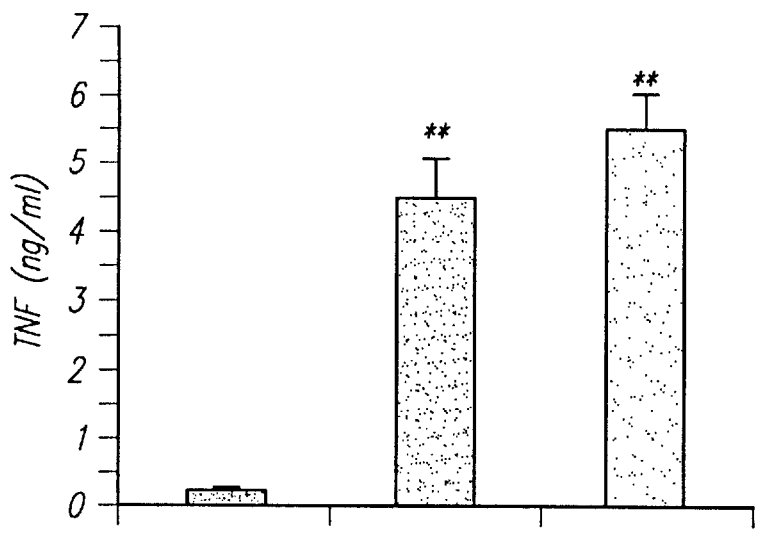
FIG. 6 represents the effect of INH$_2$BP (10 mg/kg i.p.) on the LPS-induced TNF, IL-10 and IL-6 responses in mice, at 90 min. after LPS administration (4 mg/kg i.p.). ## represents a significant effect of LPS when compared to controls (p<0.01); ## represents significant augmentation of the response by INH$_2$BP (p<0.01); n=4–5.
Figure 6B:
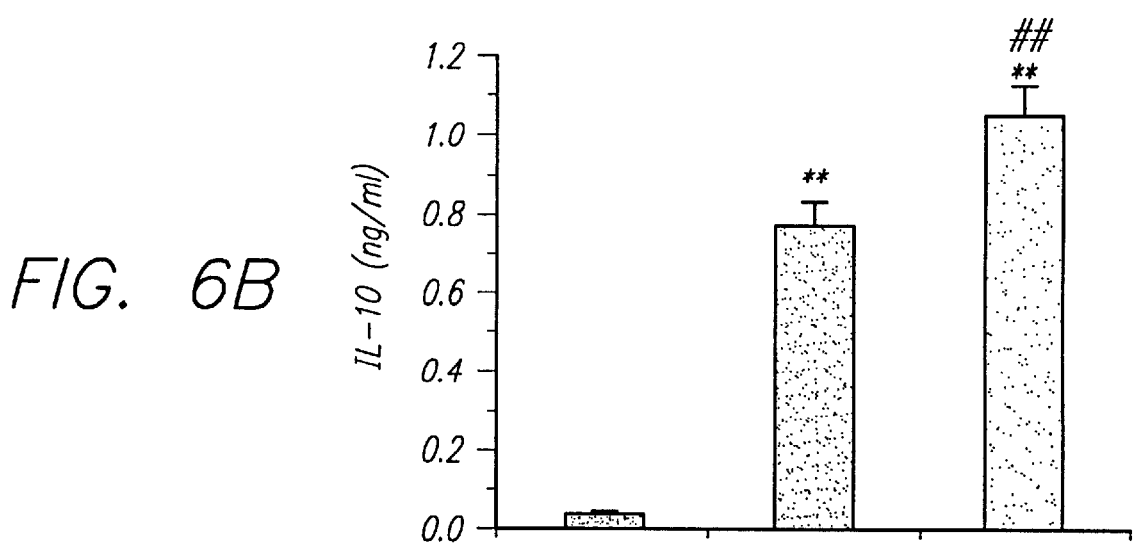
Figure 6C:
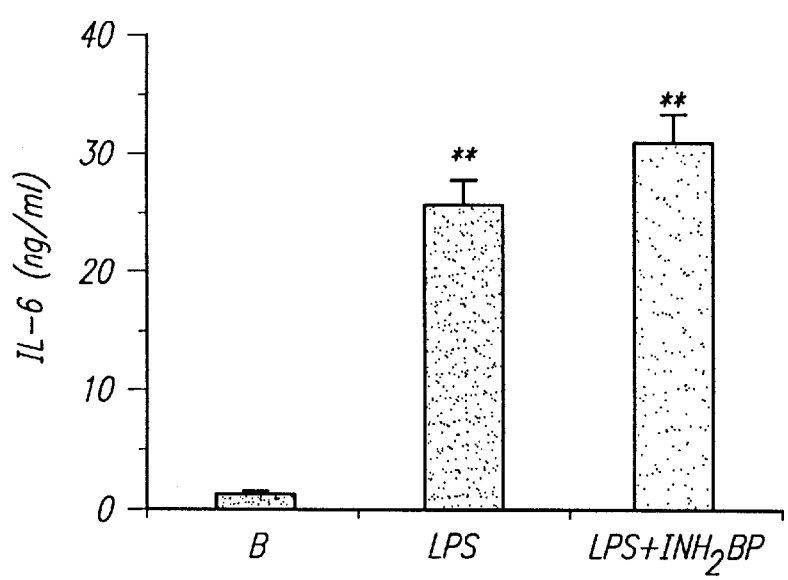

Similarly to the in vitro results (FIG. 1*c*), INH$_2$BP did not significantly affect the LPS-induced increase in plasma TNF levels in mice (FIG. 6*a*) nor did INH$_2$BP affect LPS-induced IL-6 production (FIG. 6C). However, INH$_2$BP caused an augmentation of the LPS-induced IL-10 plasma response (FIG. 6*b*).

Figure 7:
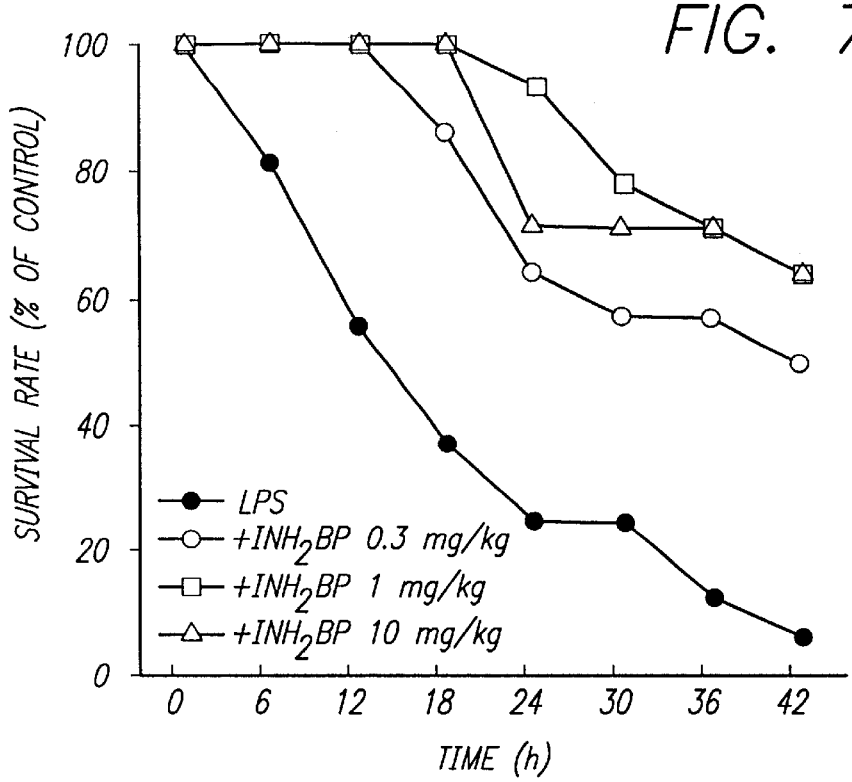
FIG. 7 represents the improved survival in INH$_2$BP treated mice subjected to endotoxin shock: effect of INH$_2$BP pretreatment (0.3–10 mg/kg) on endotoxin-induced (120 mg/kg i.p.) mortality in mice; n=7–8 animals in each group.

Pretreatment of mice by INH$_2$BP caused a significant and dose-dependent improvement in the survival rate subjected to lethal doses of LPS (FIG. 7).

INH$_2$BP suppresses the LPS-induced induction of iNOS.

The inhibitory effect of INH$_2$BP on iNOS expression was indicated by the inhibition on nitrite production, iNOS mRNA expression and iNOS protein expression. The regulation occurs in the early stage of iNOS induction, since INH$_2$BP gradually loses its effectiveness when applied at increasing times after the stimulus for iNOS induction. The regulation of INH$_2$BP of iNOS induction occurs both in vitro and in whole animals. In addition, our data show that the LPS-induced production of cyclooxygenase metabolites, similar to the induction of iNOS, is modulated by INH$_2$BP. The production of cyclooxygenase metabolites by pro-inflammatory cytokines is due to novel mRNA and protein synthesis, and expression of COX-2, by a process which shares similarities with the process of iNOS induction (Vane et al., *Inflamm. Res.* 44:1–10 (1995)). The inhibition of the LPS-induced expression of inflammatory mediators, however, is not a non-specific response to INH$_2$BP, since the induction of TNF by LPS was not affected by this agent in the J774 cells.

Interestingly, the inhibitory effect of INH$_2$BP on iNOS was greatly reduced when LPS was used in combination with INF for immunostimulation. This effect may be due to the fact that IFN-induced transcription factors such as interferon-regulatory factor (Martin et al., *J. Exp. Med.* 180:977–84 (1994)) bypass the inhibition of the iNOS induction by the above mentioned agents.

Previous in vitro studies have suggested that induction of iNOS is modulated by pharmacological inhibitors of pADPRT in macrophages in vitro (Hauschildt et al., *Biochem. J.* 288:255–260 (1992) and Pellat-Seceunyk et al., *Biochem. J.* 297:53–58 (1994)). However, in these studies, the pADPRT inhibitors aminobenzamide and nicotinamide were used at high concentrations (10–30 mM), which inhibited total protein and RNA synthesis, and may have had additional, pharmacological actions, such as free radical scavenging (Hauschildt et al., supra).

The present experiments, using INH$_2$BP, further suggest the pleiotropic involvement of pADPRT in the process of iNOS mRNA transcription. In order to study the regulation of the iNOS promoter by INH$_2$BP, transient transfection assays were performed using murine macrophage iNOS promoter luciferase constructs. These data with the deletional constructs indirectly suggest that INH$_2$BP regulates a transcription event which involves the murine iNOS promoter region between −1592 and −367 bp. ADP-ribosylation of histones and nucleases may be involved in the maintenance of a relaxed chromatin structure (Bauer et al., *Int. J. Oncol.* 8:239–252 (1995), Bauer et al., *Biochimie* 77:347–377 (1995), and Ueda et al., *Ann. Rev. Biochem.* 54:73–100 (1985)). Based on previous experimental data, it is reasonable to suggest that in these experimental systems pADPRT inhibitory compounds, e.g., INH$_2$BP, pretreatment inhibits auto-poly-ADP-ribosylation of pADPRT and histones. Such action is known to trigger the conversion of relaxed to condensed chromatin, and, by way of upregulation of nucleases and other DNA structure regulatory enzymes may affect promoter functions.

Pathophysiological and therapeutic implications; INH2BP modulates the inflammatory process at multiple levels.

Reduction by pADPRT inhibitors of the expression of pro-inflammatory genes iNOS and COX-2, and the subsequent reduced formation of NO and prostaglandins may be beneficial in various forms of inflammation. In addition, enhanced release of IL-10 may have additional anti-inflammatory actions (Liles et al.,*J. Infect Dis.* 172:1573–80 (1995), Giroir, *Critical Car. Med.* 21:780–9 (1993) and Szabo et al., *Immunology* 90:95–100 (1997)). It is conceivable that such effects significantly contribute to the improvement by pADPRT inhibitory compounds, e.g., INH$_2$BP pretreatment and the survival rate of mice challenged with lethal doses of endotoxin.

On one hand, it is conceivable that pADPRT activity or the binding of pADPRT protein is involved in the regulation of the production of inflammatory mediators and/or the expression of genes that code for components of the inflammatory process. On the other hand, it is probable that indirect down-regulation of MAP kinase activity by INH$_2$BP (Bauer et al., *Int. J. Oncol.* 8:239–252 (1995)) may also contribute to the observed effects, as predicted by other studies (Kyriakis et al., *J. Biol. Chem.* 271:24313–24316 (1996) and Ferrell, *TIBS* 21:460–466 (1996)). The present results demonstrate the therapeutic potential of pADPRT inhibitory compounds such as INH$_2$BP in various inflammatory diseases.

EXAMPLE 2

Induction and evaluation of collagen-induced arthritis

Male DBA/1J mice (9 weeks, Jackson Laboratory, Bar Harbor, Me.) were used for these studies. Chick type II collagen (CII) was dissolved in 0.01 M acetic acid at a concentration of 2 mg/ml by stirring overnight at 4° C. Dissolved CII was frozen at −70° C. until use. Complete Freund's adjuvant (CFA) was prepared by the addition of *Mycobacterium tuberculosis* H37ra at a concentration of 2 mg/ml. Before injection, CII was emulsified with an equal volume of CFA. Collagen-induced arthritis was induced as previously described by Hughes et al., *J. Immunol.* 153:3319–3325 (1994). On day 1, mice were injected intradermally at the base of the tail with 100 mL CII. On day 21, a second injection of CII in CFA was administered. Animals were treated with either vehicle (n=10) or with INH$_2$BP (n=60(0.5 g/kg p.o.) every 24 hours, starting from Day 25. Mice were evaluated daily for arthritis by using a macroscopic scoring system ranging from 0 to 4 (1—swelling and/or redness of the paw or one digit; 2—two joints involved; 3—more than two joints involved; and 4—severe arthritis of the entire paw and digits). The arthritic index for each mouse was calculated by adding the four scores of the individual paws. At the end of the experiments (Day 35), animals were sacrificed under anesthesia, and paws and knees were removed and fixed for histological examination. Histological examination was performed by an investigator blinding for the treatment regime.

Data analysis and presentation

For the studies with carrageenan-induced paw edema, paw volumes in the treated and untreated groups of animals were compared with unpaired Student's test. For the arthritis studies, Mann-Whitney U-test (2-tailed, independent) was used to test the statistical differences in the arthritic indices. This nonparametric statistic was used to compare medians, rather than means, because the scale of measurement was ordinal, and the distribution values were typically nonnormally distributed; Hughes et al., supra.

Figure 10:
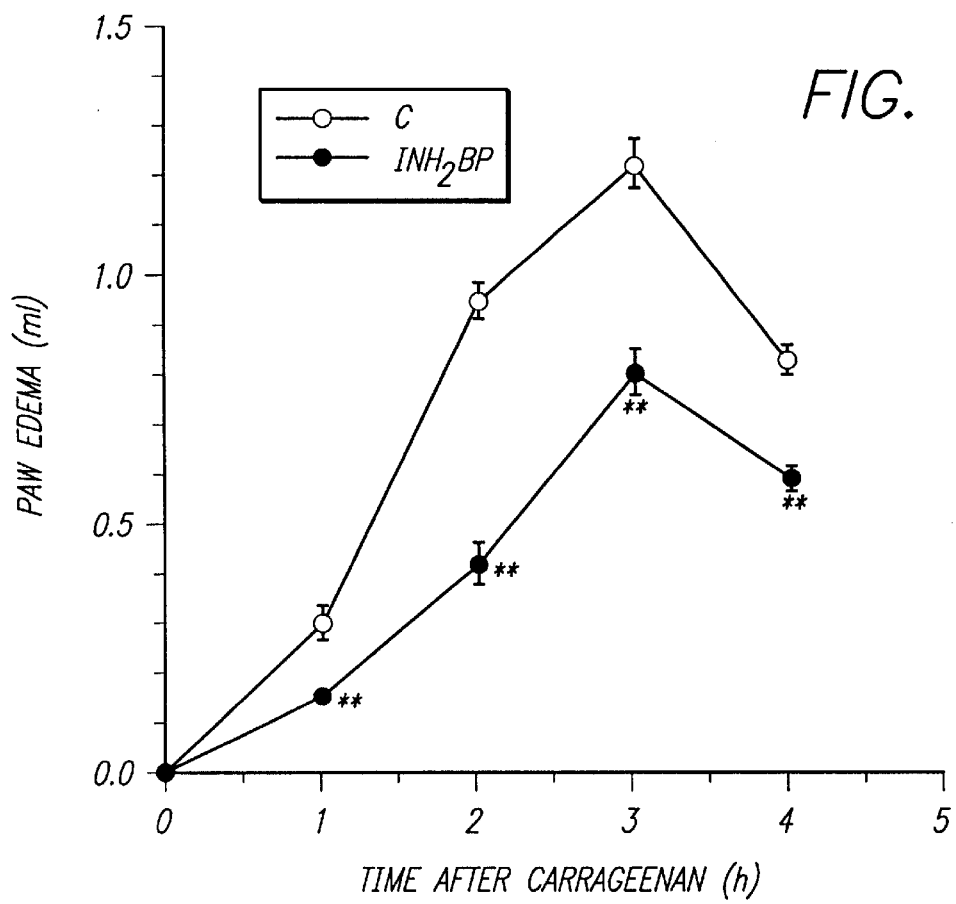
FIG. 10 describes the effect of INH$_2$BP on the development of carrageenan-induced paw edema. Data show paw volumes at 1–4 hours after carrageenan injection (means ±S.E.M., n=6 animals in each group). There was a significant increase in the paw volume from hour 1 (p<0.01), and there was a significant inhibition of the development of paw edema of $INH_2BP$ at 1–4 hours (**p<0.02).
Figure 8:
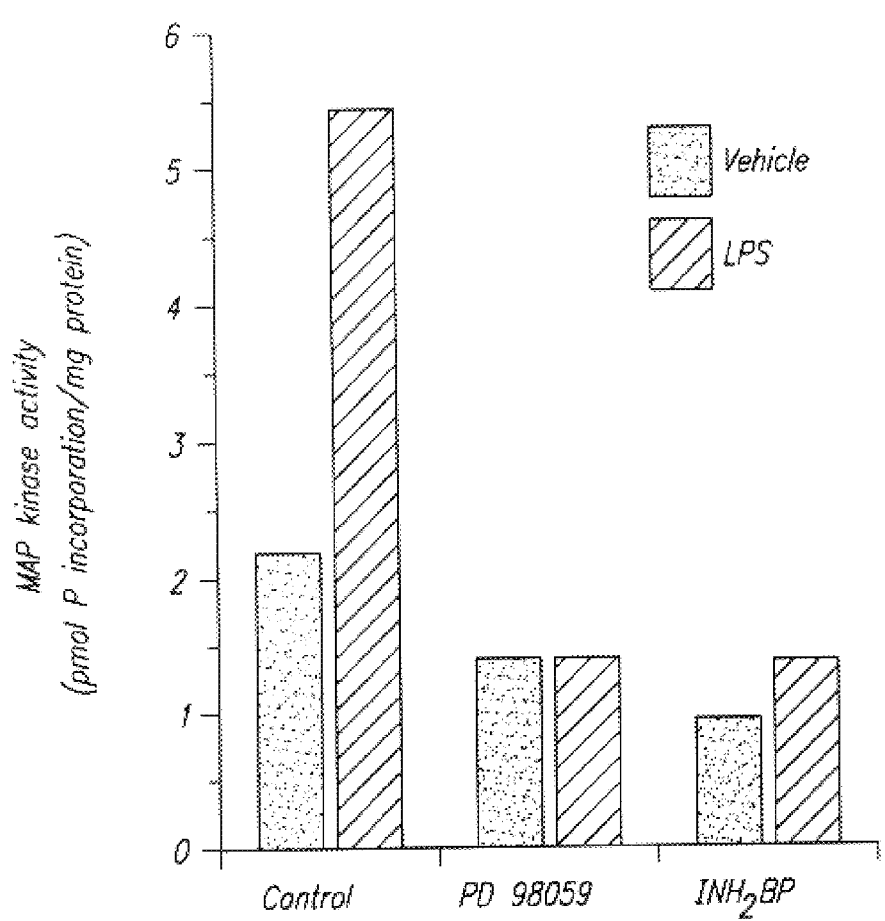
FIG. 8 (a) MAP kinase activity in RAW 264.7 cells treated with vehicle or LPS (10 μg/ml) for 24 hours in the presence or absence of 100 μM PD 98059 or 150 μM INH$_2$BP. Data represent values obtained in a typical experiment. Similar results were seen on 3 different experimental days. (b) Representative in gel MAP kinase assay in RAW 264.7 cells at 24 hours after vehicle or LPS treatment in the presence or absence of 150 μM INH$_2$BP. Lanes 1–4 represent the following groups, respectively: 1. vehicle-treated control; 2. LPS treatment; 3. vehicle treatment in the presence of 150 μM INH$_2$BP; 4: LPS treatment in the presence of 150 μM INH$_2$BP.
Figure 8:
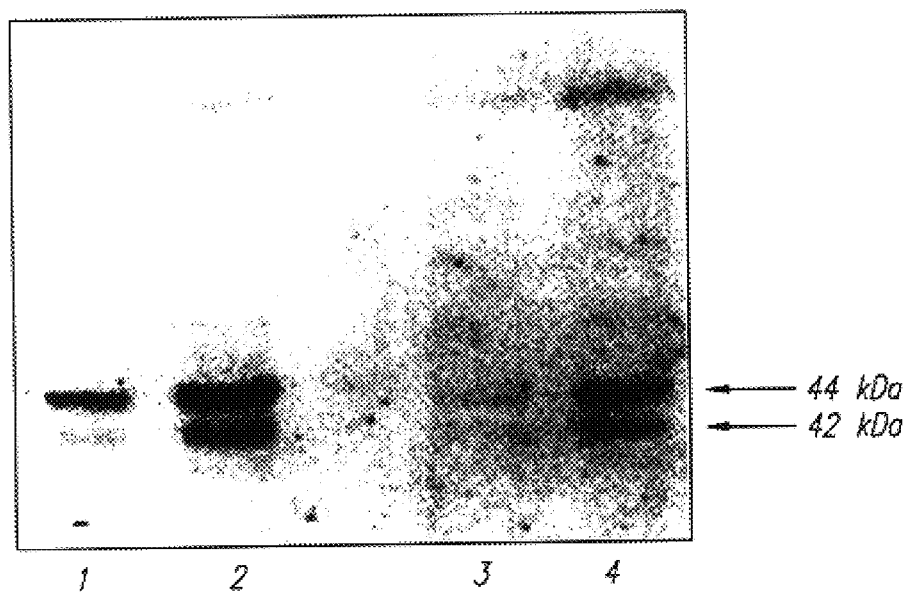
Figure 9:
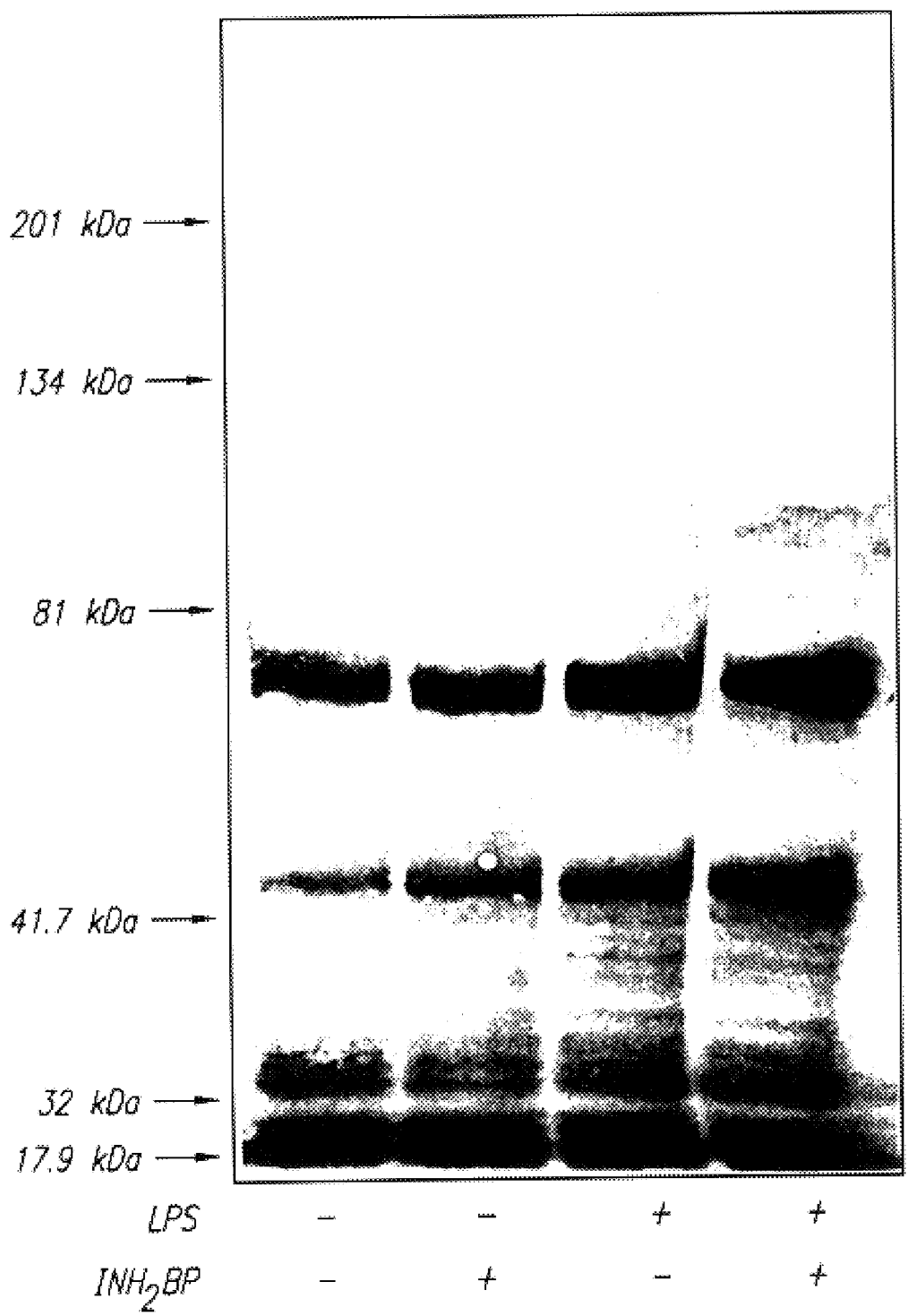
FIG. 9 describes how inhibition of pADPRT with INH$_2$BP does not alter the nuclear translocation of NF-$_K$B Western blot of nuclear extracts of control J74 cells and cells at 90 minutes after LPS treatment in the presence or absence of INH$_2$BP (100 μM).
Figure 11:
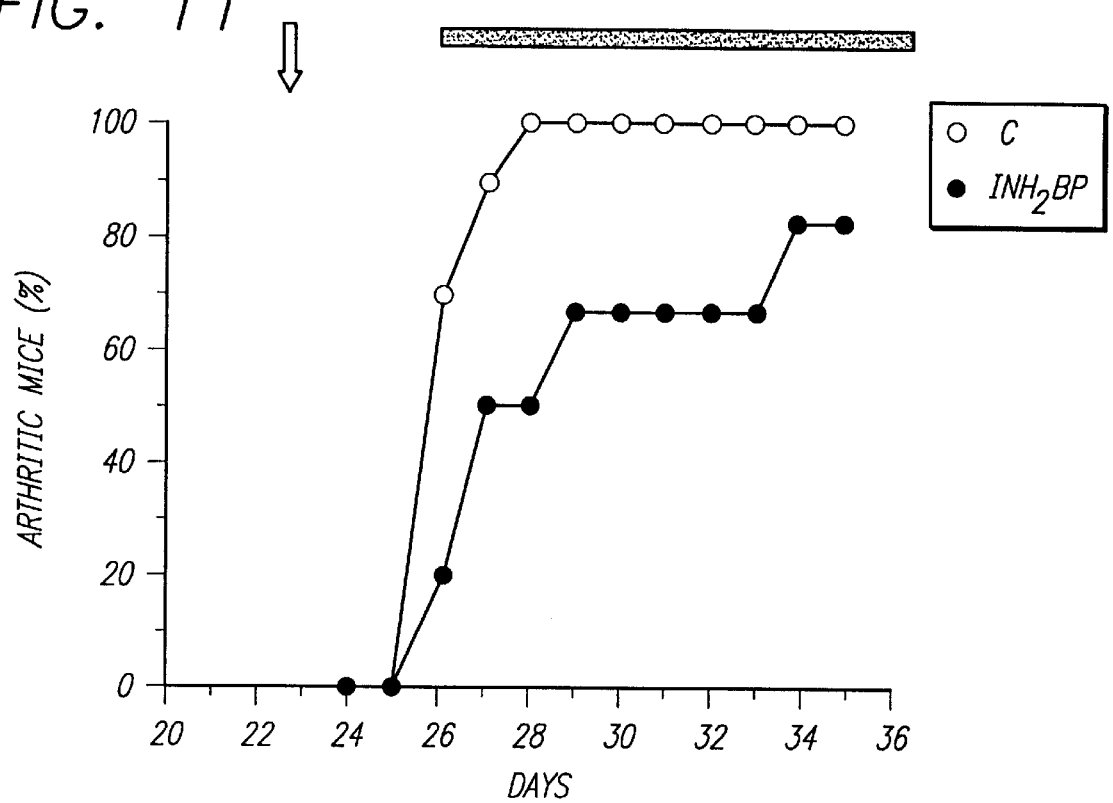
FIG. 11 describes the effect of $INH_2BP$ on the onset of collagen-induced arthritis. The percentage of arthritic mice (mice showing clinical scores of arthritis >1) are represented. The arrow at 21 days represents the time of the second collagen immunization, the horizontal bar from day 25 represents the time of the start of treatment with $INH_2BP$ (N=6) or VEHICLE (N-10).
Figure 12:
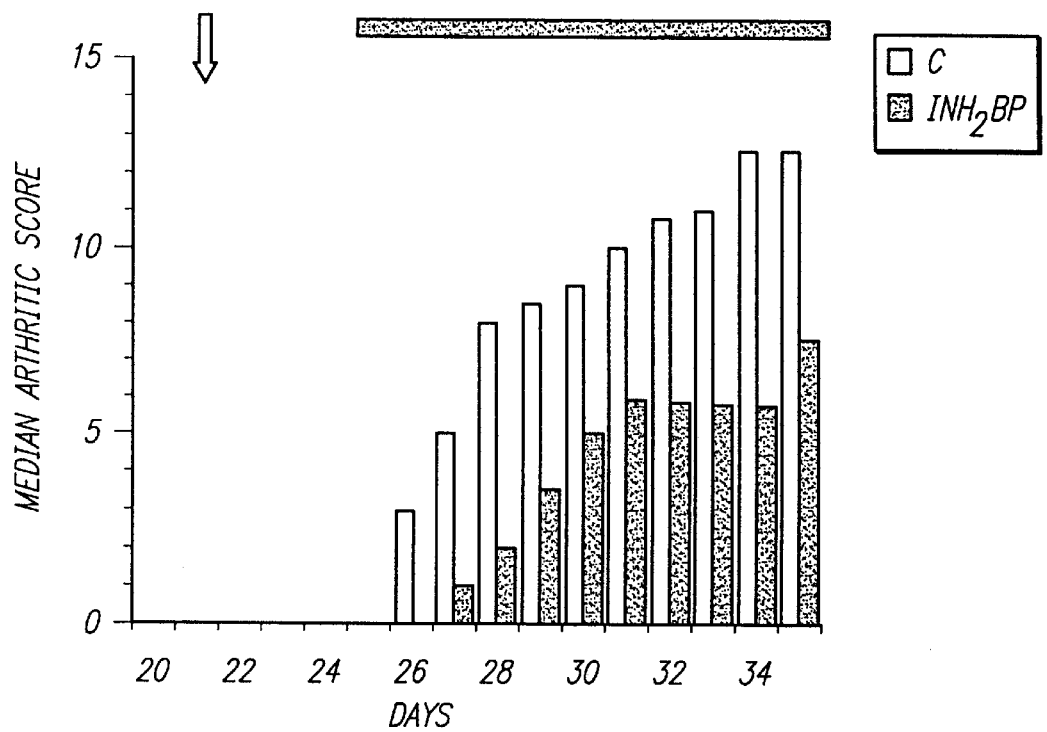
FIG. 12 describes the effect of $INH_2BP$ on the severity of collagen-induced arthritis. Median arthritic score during collagen-induced arthritis is represented. The arrow at 21 days represents the time of the second collagen immunization. The horizontal bar from day 25 represents the time of the start of treatment with $INH_2BP$ (n-6) or vehicle (n=10). There was a significant increase in the arthritic score from day 26 (Ip<0.01), and there was a significant suppression of the arthritic score by $INH_2BP$ between days 26–35 (#p<0.05).

Values in FIG. 10 are expressed as mean ±standard error of the mean of n observations, where n represents the number of rats (6 animals for each group). Values in FIG. 11 represent incidences (%), whereas values in FIG. 12 represent medians. A P-value less than 0.05 was considered statistically significant (I'<0.05; **p<0.02).

Materials 5-iodo-6-amino-1,2-benzopyrone (INH$_2$BP) was prepared as described in Example 1. Chick type II collagen was obtained from Elastin Products Company, Inc. (Owensville, Mo.). *Mycobacterium tuberculosis* H37Ra was from Difco (Detroit, Mich.). All other chemicals were from Sigma Chemical Co. (St. Louis, Mo.). Subplantar injection of carrageenan into the rat paw led to a time-dependent increase in paw volume with a maximal response at 3 hour (FIG. 10). This carrageenan induced paw edema was significantly reduced by treatment with INH$_2$BP (FIG. 10).

In the collagen-induced arthritis model in mice, between Days 26–35 after the first collagen immunization, animals progressively developed arthritis, as evidenced by an increase in the arthritis incidence and an increase in the arthritic score (FIGS. 6–7). Treatment with INH$_2$BP reduced the incidence of arthritis until Day 33 and reduced the severity of the disease throughout the experimental period. By Day 30, arthritic score increased to 10, whereas median arthritic scores in the INH$_2$BP treated animals remained around 5 (FIG. 12). By Day 35, all vehicle-treated animals, and most of the INH$_2$BP treated animals had some degree of arthritis (FIG. 11). However, even at Day 35, the median arthritic scores were significantly decreased by INH$_2$BP treatment (FIG. 12).

At Day 35, histological evaluation of the paws in the vehicle-treated arthritic animals revealed signs of severe suppurative arthritis, with massive mixed (neutrophil, macrophages and lymphocyte) infiltration into the larger ankle joints and the terminal digits. In addition, a severe or moderate necrosis, hyperplasia and sloughing of the synovium could be seen, together with the extension of the inflammation into the adjacent musculature with fibrosis and increased mucous production. In the animals treated with INH$_2$BP, the degree of arthritis was significantly reduced. Nevertheless, there was still a significant degree of arthritis in these animals, with a moderate, primarily neutrophil infiltration into several of the larger joints, coupled with mild to moderate necrosis and hyperplasia of the synovium. Similar to these findings in the paw, signs of severe suppurative arthritis were found in the knee, which was reduced by treatment with INH$_2$BP (not shown).

Discussion

NO, peroxynitrite, oxyradicals and products of the inducible cyclooxygenase have independently been proposed as important factors in the pathogenesis of various forms of inflammation, including arthritis (Brahn, *Clin. Orthop. Rel. Res.* 265:42–53 (1991); Kaur et al., *FEBS Lett.* 1359:9–12 (1994); Oyanagui Y, *Life Sci.* 54:PL285–9 (1994); Miesel et al., *Inflammation* 6:597–612 (1994); Whiteman et al., *Annals. of the Rheumatic Diseases* 55:383–7 (1996); Anderson et al., *J. Clin. Invest.* 97:2672–2679 (1996)). The present study, demonstrating anti-inflammatory effects of INH$_2$BP in the carrageenan-induced paw edema model and in the collagen induced arthritis model supports the view that PARS is involved in the progression of the inflammatory process and the pharmacological inhibition of PARS is of anti-inflammatory potential.

The overproduction of NO in inflammatory conditions is due to the suppression of the inducible isoform of NOS (iNOS). Several lines of evidence suggest a role for iNOS and NO overproduction in the pathogenesis of arthritis (Stenovic-Racic, et al., *Arthr. Rhemat.* 36:1036–1044 (1993)). First, the expression of iNOS and the production of large amounts of NO has been demonstrated in chondrocytes from experimental animals and humans (Haeselmann et al., *FEBS Lett.* 352:361–364 (1994); Sakurai et al., *J. Clin. Invest.* 96:2357–63 (1995); Grabowski et al., *Br. J. Rheumatol.* 35:207–12 (1996); Murrell et al., *J. Bone Joint Sur.—Am.* 78:265–74 (1996). Second, an increase in the circulating levels of nitrite/nitrate (the breakdown products of NO) has been demonstrated in patients with arthritis (Farrell et al., *Ann. Rhem. Dis.* 51:1219–22 (1992); Stichtenoth, et al., *Ann. Rhem. Dis.* 54:820–4 (1995). Third, the development of arthritis has been shown to be reduced by non-isoform-selective inhibitors of NOS (McCartney-Francis et al., *J. Exp. Med.* 178:749–753 (1993); Weinberg et al., *J. Exp. Med.* 1979:651–60 (1994); Stefanovic-Racic et al., *Arthr. Rheumat.* 37:1062–9 (1994); and, more recently, by inhibitors with selectivity for iNOS (Connor et al., *Eur. J. Pharmacol.* 273:15–24 (1995).

In this respect it is noteworthy that pretreatment of multiple cell types with PARS inhibitors (including 3-aminobenzaminde, nicotinamide as well as INH$_2$BP) prior to immunostimulation has been shown to suppress the expression of mRNA for iNOS and reduce NO production (Zingarelli et al *J. Immunol.* 156:350–358 (1996)). From these experimental data it may be concluded that PARS via a not yet characterized mechanism, also regulates the process of iNOS expression, and that this effect may represent an additional mode of beneficial action of PARS inhibition in various forms of inflammation. In the in vitro studies cited above, extremely high concentrations of the PARS inhibitors 3-amiobenzamide and nicotinamide were required (10–30 mM) in order to demonstrate suppression of iNOS induction. These high concentrations of these agents may have additional pharmacological actions, such as inhibition of total protein and RNA synthesis, and/or free radical scavenging actions (Zingarelli et al., supra). INH$_2$BP, on the other hand, effectively suppressed the expression of iNOS even at lower, non-cytotoxic concentrations (100–300 mM).

EXAMPLE 3

Protection against peroxynitrite-induced fibroblast injury and arthritis development by inhibition of poly (ADP-ribose) synthetase Cell culture Mouse embryo fibroblasts from a PARS$^{-/-}$ mouse (a genetically engineered mouse that lacks the gene for PARS) and fibroblasts from a corresponding wild-type control (Wang et al., (1995) *Genes Develop.* 9: 510–520) were grown in Dulbecco's modified Eagle's Medium with 10% fetal bovine serum. Cells were cultured in 96-well plates or in 12-well plates until 90% confluence. Cells were exposed to peroxynitrite (25–1000 μM) in the presence or absence of a 10 min pretreatment with INH$_2$BP (100 μM). For immunostimulation, cells were exposed to bacterial lipopolysaccharide (LPS, 10 μg/ml) and murine gamma-interferon (IFN, 50 U/ml) for 2–48 hours in the presence or absence of INH$_2$BP (50–100 μM). INH$_2$BP was synthesized as described in Example 1.

Determination of DNA single strand breaks and measurement of cellular PARS activity At 10 min after peroxynitrite exposure, the formation of DNA single strand breaks in double-stranded DNA was determined by the alkaline unwinding method as previously described by Szabó, C. (1996) *Shock* 6: 79–88; Szabó et al., (1996) *Proc. Natl. Acad. Sci. USA* 93: 1753–1758. PARS activity was measured 10 min after peroxynitrite exposure, using radiolabeled NAD$^+$ as described, in digitonin-permeabilized cells.

Measurement of mitochondrial respiration and cellular NAD+ levels.

At 60 min after peroxynitrite exposure or 48 h after immunostimulation, respiration was assessed by the mitochondrial-dependent reduction of MTT [3-(4,5-dimethylthiazol-2-yl)-2,5-diphenyltetrazolium bromide] to formazan as described by Szabó et al., supra, referenced in Example 1. In addition, in some experiments, cellular $NAD^+$ levels were determined using HPLC.

Measurement of nitrite or nitrite/nitrate production, iNOS mRNA and iNOS protein expression by immunostimulated cells.

Nitrite in culture supernatants at 24 hours after stimulation was measured by the Griess reaction as described by Szabó et al., Circ. Res. 78:1051–1063 (1996). For the determination of total nitrite/nitrate concentrations, nitrate was reduced to nitrite by incubation with nitrate reductase. After exposing cells to LPS/IFN in the presence or absence of $INH_2BP$ (100 μM) for 1–24 hours, Northern blotting for iNOS mRNA and Western blotting for iNOS protein, using a primary rabbit anti-mouse iNOS antibody (Upstate Biotechnology, Lake Placid, N.Y.) were performed as described (Zingarelli et al., J. Immunol. 156:350–358 (1996)). The activity of iNOS in cell homogenates was determined by the measurement of the calcium-independent conversion of L-arginine to L-citrulline.

Effect of $INH_2BP$ on peroxynitrite- and hydrogen peroxide-induced oxidation of dihydrorhodamine 123.

The effect of $INH_2BP$ and the conventional PARS inhibitor 3-aminobenzamide (100 μM–3 mM) on the peroxynitrite-mediated oxidation of dihydrorhodamine 123 was studied in vitro. These studies were performed in phosphate-buffered saline (PBS) containing 100 μM diethylenepentaacetic acid (DTPA), pH 7.4. The oxidation of DHR 123 by peroxynitrite (1 μM) or hydrogen peroxide (1 μM) plus 25 μg/ml horseradish peroxidase in the presence of various concentrations of the PARS inhibitors was measured by the change in absorbance at 500 nm ($\gamma=78,000$ $M^{-1}$ $cm^{-1}$) after 30 min incubation at 37° C.

Induction of collagen-induced arthritis, and detection of nitrotyrosine in the inflamed joints Male DBA/1J mice (9 weeks, Jackson Laboratory, Bar Harbor, Me.) were used for these studies. Chick type II collagen (CII) was dissolved in 0.01 M acetic acid at a concentration of 2 mg/ml by stirring overnight at 4° C. Dissolved CII was frozen at −70° C. until use. Complete Freund's adjuvant (CFA) was prepared by the addition of *Mycobacterium tuberculosis* H37Ra at a concentration of 2 mg/ml. Before injection, CII was emulsified with an equal volume of CFA. Collagen-induced arthritis was induced as previously described (Hughes et al., J. Immunol. 153: 3319–3325 (1994)). On day 1, mice were injected intradermally at the base of the tail with 100 μl of the emulsion (containing 100 μg CII). On day 21, a second injection of CII in CFA was administered. At Day 35, joints were taken, embedded in M1 medium and snap frozen in liquid nitrogen. Cryostat sections (6 μm) were cut with a microtome equipped with a carbide steel knife. Joint sections were analyzed for the presence of nitrotyrosine, an indicator of peroxynitrite by immunohistochemistry as described, using a primary anti-nitrotyrosine antibody (Upstate Biotech, Saranac Lake, N.Y.). In control experiment, sections were incubated in the presence of 10 mM nitrotyrosine. This intervention eliminated the nitrotyrosine staining presented in FIG. 16.

In another set of studies, aqueous joint extracts were prepared from control animals and from animals at 35 days of arthritis as described by Kasama et al., J. Clin. Invest. 95: 2868–2876 (1995), by homogenization in a lysis buffer in the presence of protease inhibitors. Extracts were analyzed for the presence of nitrated proteins, using Western blotting, as described by Cuzzocrea et al., Br. J. Pharmacol. 122: 493–503 (1997).

Induction of collagen-induced arthritis, and its suppression by $INH_2BP$

In another set of experiments, PARS was inhibited in the animals with $INH_2BP$. Animals were treated with either vehicle (n=10) or with $INH_2BP$ (n=6) (0.5 g/kg p.o.) every 24 hours, starting from Day 25. Experiments with $^{14}$C-labeled $INH_2BP$ have established that the dosage regimen used in this study provides adequate tissue uptake of the PARS inhibitor (Bauer et al., Int. J. Oncol. 8: 239–252 (1996)). Mice were evaluated daily for arthritis by using a macroscopic scoring system: 0=no signs of arthritis; 1=swelling and/or redness of the paw or one digit; 2=two joints involved; 3=more than two joints involved; and 4=severe arthritis of the entire paw and digits. Id. Arthritic index for each mouse was calculated by adding the four scores of individual paws. At Day 35, animals were sacrificed under anesthesia, and paws and knees were removed and fixed for histological examination, which was done by an investigator blinded for the treatment regime.

Data analysis and presentation.

For the in vitro studies, all values in the figures and text are expressed as mean ±standard error of the mean of n observations, where n represents the number of wells studied (6–9 wells from 2–3 independent experiments). Data sets were examined by one-and two-way analysis of variance and individual group means were then compared with Student's unpaired t-test. For the arthritis studies, Mann-Whitney U-test (2-tailed, independent) was used to compare medians of the arthritic indices. Values in for the in vitro studies are presented as incidences (%), or medians. A p-value less than 0.05 was considered statistically significant.

Results

Role of PARS activation in the peroxynitrite-mediated inhibition of mitochondrial respiration in fibroblasts.

Figure 13A:
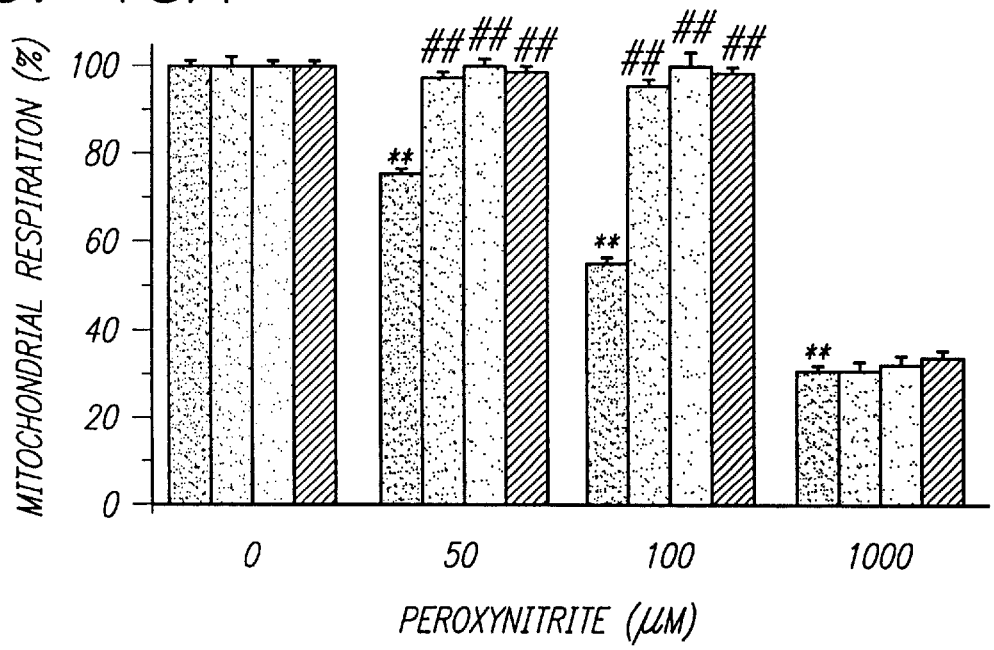
FIG. 13 describes the effect of peroxynitrite (50–1000 $\mu M$) on mitochondrial respiration (a) and PARS activity (b) in $PARS^{+/+}$ and $PARS^{-/-}$ fibroblasts (i.e. the effect of $INH_2BP$ (100 $\mu M$) in both cell types). *,** represents significant effects of peroxynitrite in $PARS^{+/+}$ cells when compared to unstimulated controls (p<0.05, p<0.01, respectively). #,## represents significant effect of $INH_2BP$ in the presence of peroxynitrite (p<0.05, p<0.01, respectively); n=6–9.
Figure 13B:
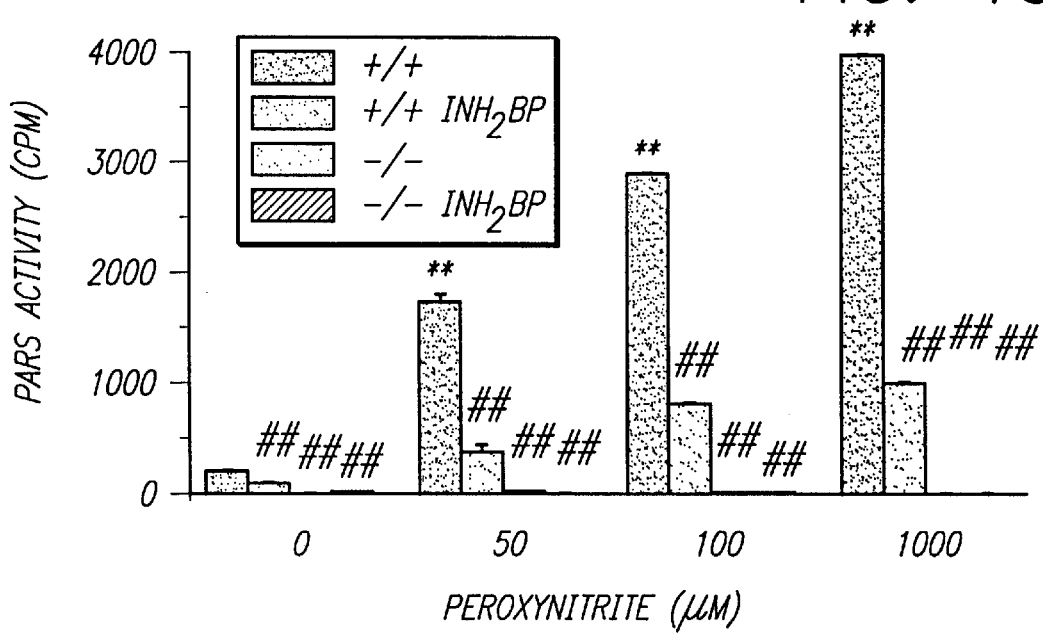

Exposure of wild-type ($PARS^{+/+}$) fibroblasts to peroxynitrite (50–1000 μM) caused a dose-dependent suppression of the mitochondrial respiration at 1 h (FIG. 13a). In addition, peroxynitrite dose-dependently increased the percentage of single-strand breaks of the DNA in these cells. For instance, at 100 μM peroxynitrite, the percentage of single strand breaks increased from 3±2% to 28±2% (p<0.01) (n=6). Peroxynitrite also caused a dose-dependent activation of PARS (FIG. 13b), with some basal PARS activity detectable in unstimulated wild-type cells (FIG. 13b). $INH_2BP$ prevented PARS activation in response to peroxynitrite (FIG. 13b), without affecting the extent of DNA single strand breakage (not shown). Pharmacological inhibition of PARS caused a significant protection against the peroxynitrite-induced suppression of mitochondrial respiration at 50 μM, 100 μM (FIG. 13a) and 250 μM (not shown) peroxynitrite. However, when cells were exposed to very high concentrations of peroxynitrite (1000 μM), the suppression of mitochondrial respiration could no longer be prevented by pharmacological inhibition of PARS, indicating non-specific cellular damage (FIG. 13a). The extent of DNA single strand breakage in the $PARS^{-/-}$ cells was similar to the DNA single strand breakage in the $PARS^{+/+}$ controls. For instance, at 100 μM peroxynitrite, the percentage of single strand breaks increased from 3±2% to 31±4% in these cells (p<0.01)

(n=6). When the cellular responses in the fibroblast line derived from the PARS$^{-/-}$ mice were compared to the response in the corresponding wild-type cells, the results were similar to what we have observed with the pharmacological inhibitor, INH$_2$BP. Cells from the PARS$^{-/-}$ mice were protected against peroxynitrite-induced suppression of mitochondrial respiration (without adding INH$_2$BP) (FIG. 13). This protection diminished when extremely high peroxynitrite concentrations were used (e.g. 1000 $\mu$M). The PARS$^{-/-}$ cells were also protected against the peroxynitrite-induced suppression of cellular NAD$^+$ levels. For instance, 100 $\mu$M peroxynitrite caused a complete depletion of cellular NAD$^+$ in the wild-type cells from (8.2±1.6 to 0.1±0.1 nmoles/mg protein; p<0.01, n=3); whereas NAD$^+$ was well maintained in the PARS$^{-/-}$ cells (control: 9.9±0.5 nmoles/mg protein; after 100 $\mu$M peroxynitrite exposure: 5.0±0.9 nmoles/mg protein). Even at very high concentrations of peroxynitrite, where no protection against the suppression of mitochondrial respiration was provided in the PARS$^{-/-}$ phenotype, cellular NAD$^+$ levels in the PARS$^{-/-}$ cells were relatively maintained. For instance, in response to 1000 $\mu$M peroxynitrite, cellular NAD$^+$ was 5.1±0.9 nmoles/mg protein in the PARS$^{-/-}$ cells (n=3). These results demonstrate that PARS activation plays an important role in the cellular injury at low to intermediate concentrations of peroxynitrite. However, at extremely high oxidant concentrations, overwhelming PARS-independent mechanisms of cytotoxicity become activated. This latter finding is in accordance with observations in pancreatic islet cells, macrophages and endothelial cells, where extremely high concentrations of oxidants caused massive cytotoxicity, which was no longer preventable by pharmacological inhibition of PARS (Szabo et al., *Proc. Natl. Acad. Sci. USA* 93:1753–1758 (1996); Szabo et al., *FEBS Lett.* 372:229–232 (1995); Kasama et al., *J. Clin. Invest.* 95:2868–2876 (1995)).

Figure 14:
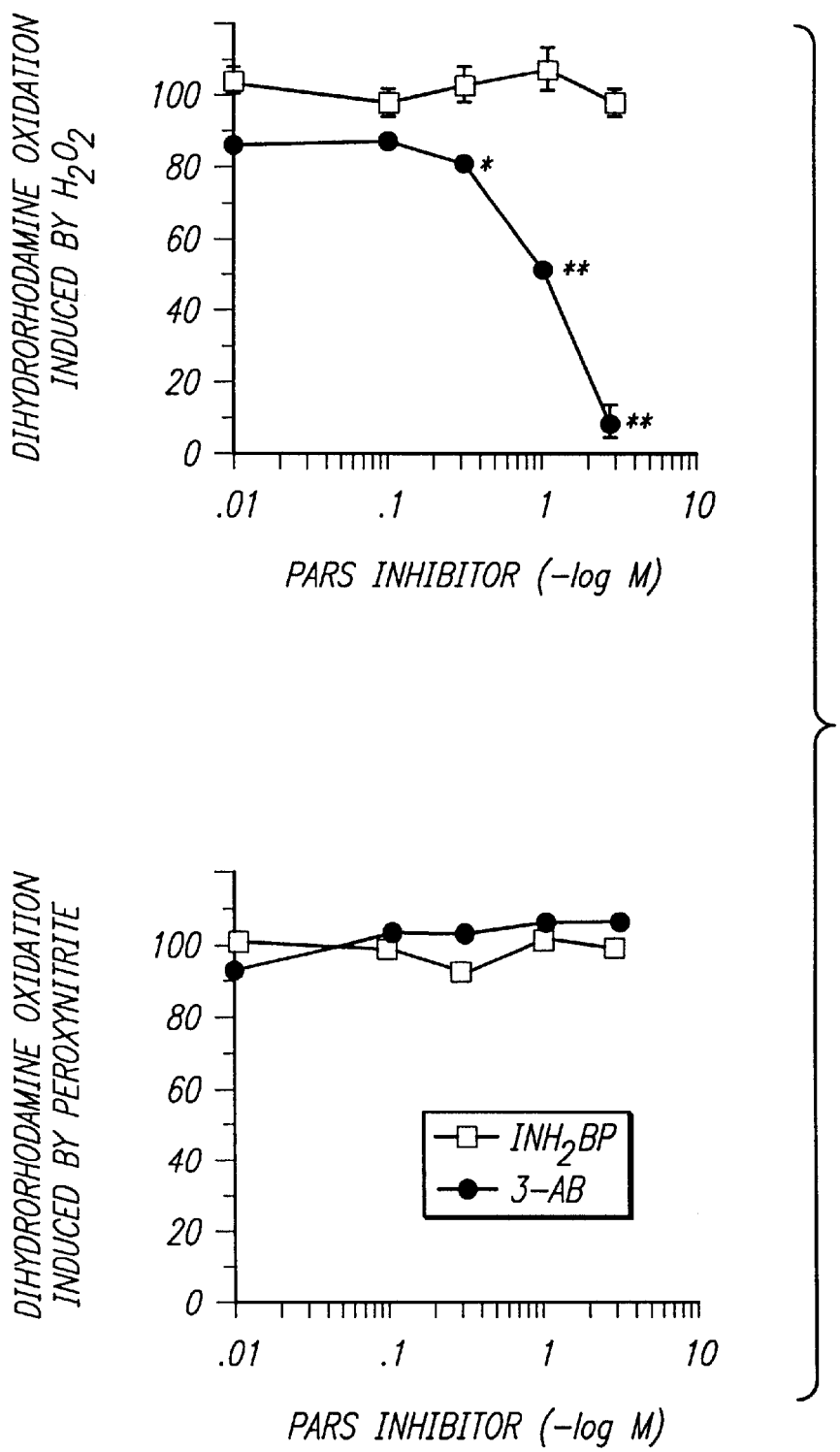
FIG. 14 describes the effect of $INH_2BP$ and 3-aminobenzamide on the oxidation of dihydrorhodamine 123 by hydrogen peroxide (top panel) or peroxynitrite (bottom panel). *,** represents significant inhibition of dihydrorhodamine oxidation by 3-aminobenzamide in response to hydrogen peroxide (p<0.05, p<0.01, respectively; n=6).

In order to directly investigate any potential scavenging effect of INH$_2$BP, in vitro studies were performed with INH$_2$BP, and 3-aminobenzamide, a prototypical PARS inhibitor, in an assay which utilizes the peroxynitrite- or hydrogen peroxide induced oxidation of dihydrorhodamine 123. The results showed that INH$_2$BP does not inhibit the peroxynitrite- or hydrogen peroxide induced oxidation, whereas in line with previous studies, 3-aminobenzamide dose-dependently inhibited the oxidation of dihydrorhodamine induced by hydrogen peroxide, but not by peroxynitrite (FIG. 14). These observations, coupled with the finding that in the PARS$^{-/-}$ cells, which resisted the suppression of mitochondrial respiration at low to intermediate concentrations of peroxynitrite, INH$_2$BP did not provide any non-specific additional protection (FIG. 13a), indicate that INH$_2$BP does not act as a scavenger of peroxynitrite.

Role of PARS in the regulation of NO production in response to immunostimulation.

Figure 15A:
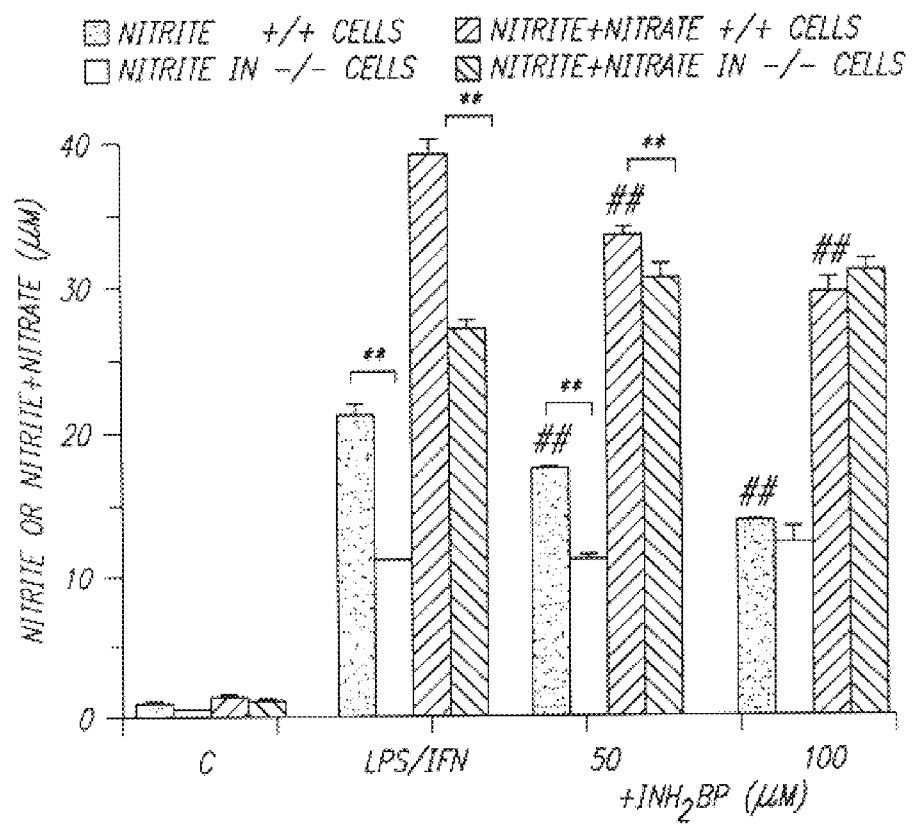
FIG. 15 represents (a) concentrations of nitrite (solid bars) or nitrite and nitrate (hatched bars), in $PARS^{+/+}$ and $PARS^{-/-}$ fibroblasts immunostimulated with LPS/IFN for 24 hours; effect of $INH_2BP$ (50–100 $\mu M$). ** represents significant effects of immunostimulation when compared to unstimulated controls (p<0.01), ## represents significant effect of $INH_2BP$ in the $PARS^{+/+}$ cells (p<0.01); n=6–9. (b) Comparison of the level of iNOS mRNA (at 2, 8, 12 and 24 h) and iNOS protein (at 12 h) expression in $PARS^{+/+}$ and $PARS^{-/-}$ cells in response to stimulation with IFN and LPS. Representative blots of n=3–4 experiments are shown.

Stimulation of the cells with LPS and interferon-gamma induced the production of nitrite and nitrate (breakdown products of NO, produced by the inducible NO synthase enzyme, iNOS) in the fibroblasts, as measured at 24 hours. There was a significantly lower nitrite and nitrate production in response to immunostimulation in the PARS$^{-/-}$ cells, when compared to wild-type controls. INH$_2$BP (50–100 $\mu$M) caused a dose-dependent inhibition of nitrite and nitrate production in the wild-type cells, lowering it to the level found in the PARS$^{-/-}$ cells (FIG. 15a). INH$_2$BP, however, did not inhibit NO production in the PARS$^{-/-}$ cells (FIG. 15a). Similar differences in the NO production persisted at 48 hours after immunostimulation.

Figure 15B:
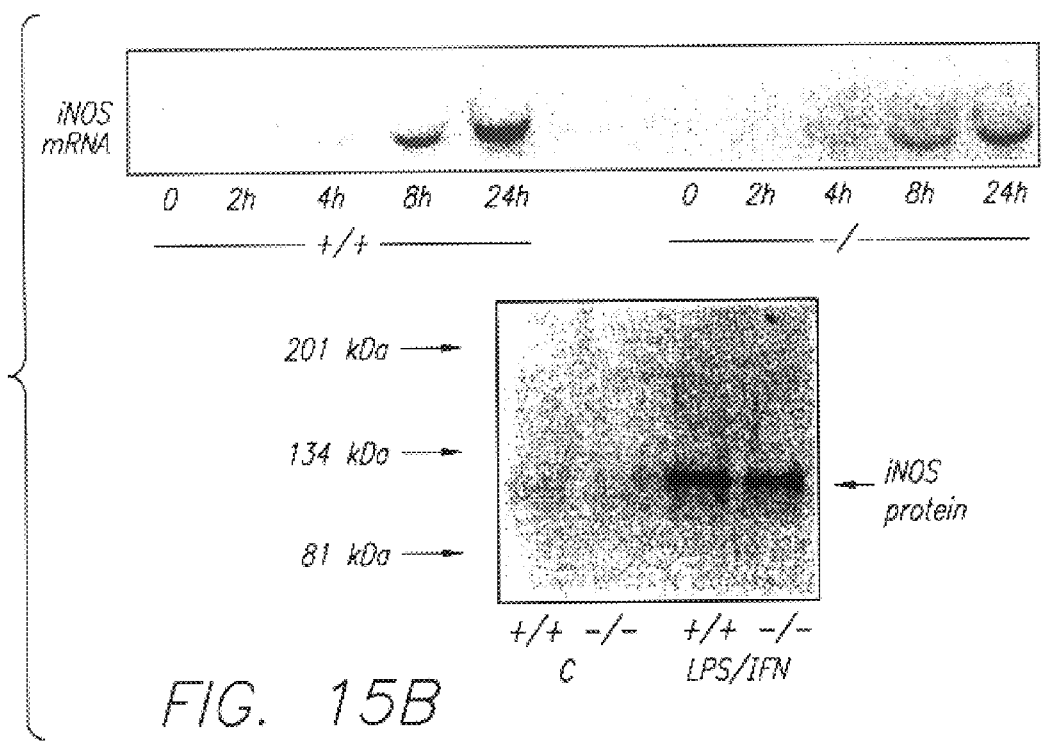

In the PARS$^{-/-}$ cells, there was a significantly lower expression of iNOS, as indicated by lower amounts of iNOS steady-state mRNA and iNOS protein levels (FIG. 15b). The mRNA for iNOS was 2.8±0.7 fold higher at 8 hours after immunostimulation and 4.6±1.9 fold higher at 24 hours after immunostimulation in the PARS$^{+/+}$ cells, than in the PARS$^{+/+}$ cells (n=3; p<0.01). Direct measurements of iNOS activity in immunostimulated cells confirmed these results: at 12 hours after immunostimulation, calcium-independent iNOS activity amounted to 306±39 nmoles/mg/min in PARS$^{+/+}$ cells, 95±11 nmoles/mg/min in INH$_2$BP pretreated PARS$^{+/+}$ cells, 90±24 nmoles/mg/min in PARS$^{-/-}$ cells and 76±38 nmoles/mg/min in INH$_2$BP pretreated PARS$^{-/-}$ cells (n=6). The lack of effect of INH$_2$BP in the PARS$^{-/-}$ cells reiterates that this agent does not exert PARS-independent cellular actions.

At 48 hours after immunostimulation, changes in mitochondrial respiration in PARS$^{+/+}$ and PARS$^{-/-}$ cells were also compared. There was a 46±6% inhibition of the respiration in response to LPS/IFN in the PARS$^{+/+}$ cells (p<0.01, n=12), whereas in the PARS$^{-/-}$ cells, no suppression of mitochondrial respiration was observed: the respiration amounted to 114±8% of the unstimulated controls (n=12, p<0.01).

Effect of INH$_2$BP in the development of collagen-induced arthritis.

Figure 16A:
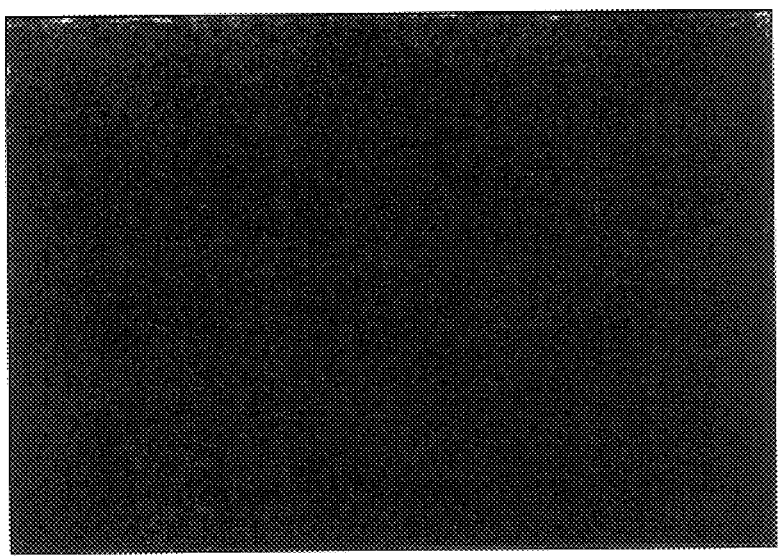
FIG. 16 represents nitrotyrosine immunostaining in (a) the paw of a control mouse and (b) the paw of a mouse at 35 days after collagen-induced arthritis. Part (c) represents nitrotyrosine Western blots from paw extracts of control mice (C) and mice after 35 days of collagen-induced arthritis (A) are shown. Note the marked increase in nitrotyrosine staining in the paws in arthritis. Also, note the increased tyrosine nitration of several proteins (indicated with arrowheads): three proteins (Mw: approx. 60–80 kDa), and a low molecular weight protein or protein fragment (Mw: approx. 10 kDa). Representative pictures or gels of n=3 experiments are shown. For parts (a) and (b), magnification: ×40.
Figure 16B:
Figure 16C:
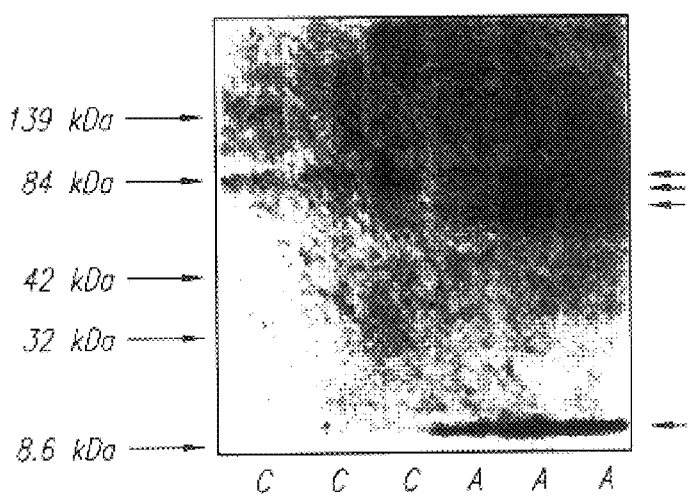

NOS inhibitors and superoxide dismutase mimics exert protective effects in rodent models of arthritis, induced by adjuvant (McCartney-Francis et al., *J. Exp. Med.* 178:749–753; Stefanovic-Racic et al., *Arthr. Rheumat.* 37:1062–1069 (1994)) or collagen (Brahn et al., *FASEB J.* 11:A530 (1997)). Using immunohistochemistry, and Western blotting of proteins in aqueous joint extracts, we observed the appearance of nitrotyrosine-positive staining in the inflamed joints, but not in healthy animals (FIG. 16). These findings are in accordance with a recent study in human samples from arthritic patients (Kaur et al., *FEBS Lett.* 350:9–12 (1994)). Nitrotyrosine formation is generally accepted as a specific "footprint" of peroxynitrite (Beckman et al., *Am. J. Physiol.* 271:C1424–1437 (1996); Ischiropoulos et al., *Arch. Biochem. Biophys.* 298:431–437 (1992)), although recent studies proposed additional pathways of tyrosine nitration, such as the one related to the myeloperoxidase-dependent conversion of nitrite to NO$_2$Cl and NO$_2$ (Eiserich et al., Nature, in press). Thus, nitrotyrosine may rather serve as a collective indicator of "reactive nitrogen species" (Halliwell, *FEBS Lett.* 411:157–160 (1997)).

Figure 17A:
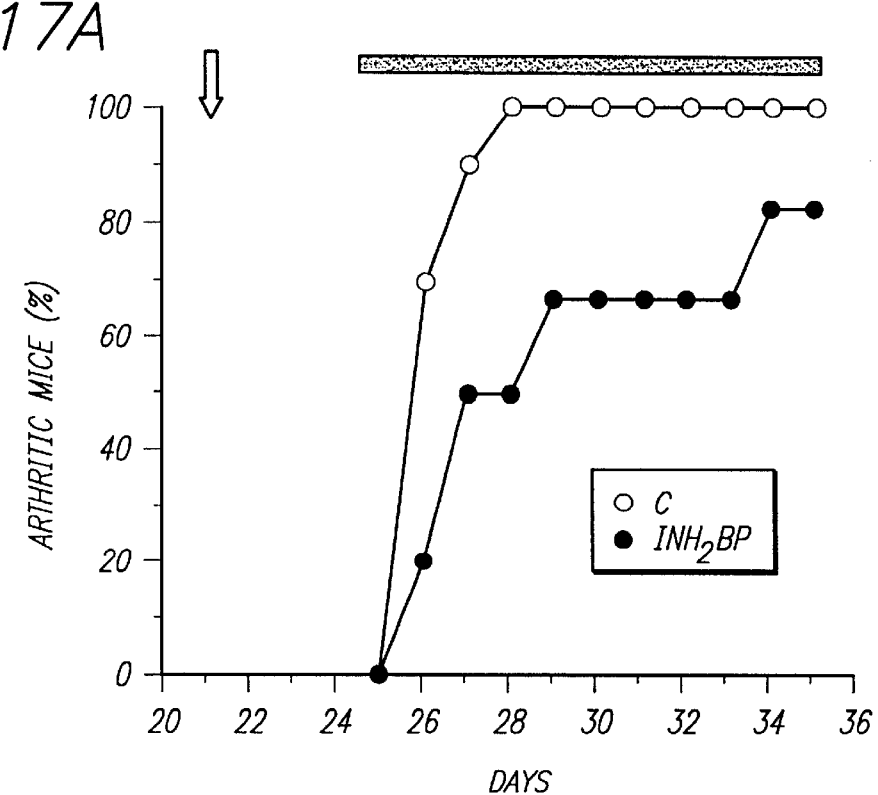
FIG. 17 represents the (A) Effect of $INH_2BP$ on the onset of collagen-induced arthritis. The percentage of arthritic mice (mice showing clinical scores of arthritis >1) are represented. (B) represents the effect of $INH_2BP$ on the severity of collagen-induced arthritis. Median arthritic score during collagen-induced arthritis is represented. The arrow at 21 days represents the time of the second collagen immunization. The horizontal bar from day 25 represents the time of the start of treatment with $INH_2BP$ (n=6) or vehicle (control; C) (n=10). There was a significant increase in the arthritic score from day 26 (*p<0.01), and there was a significant suppression of the arthritic score by $INH_2BP$ between days 26–35 (#p<0.05).
Figure 17B:
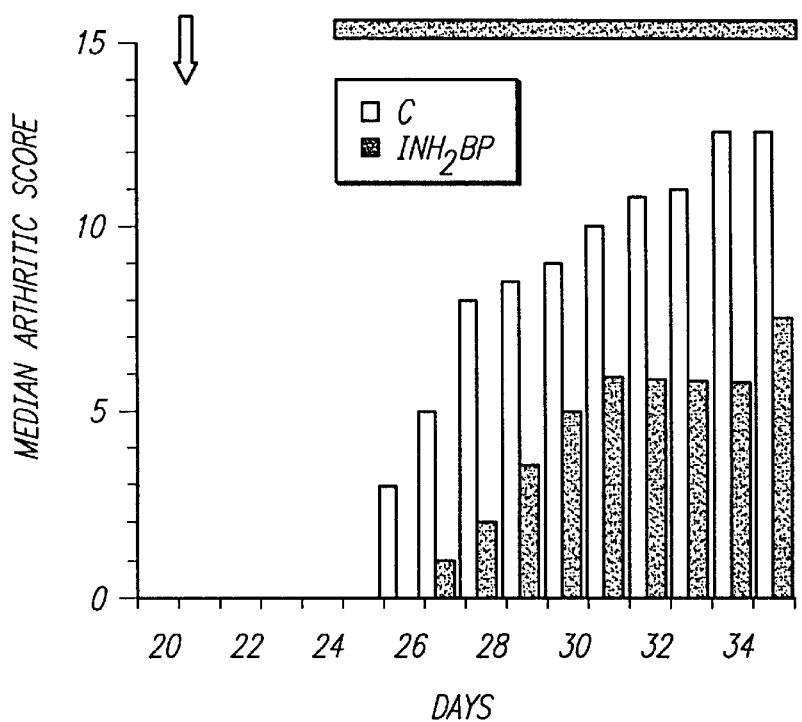
Figure 18A:
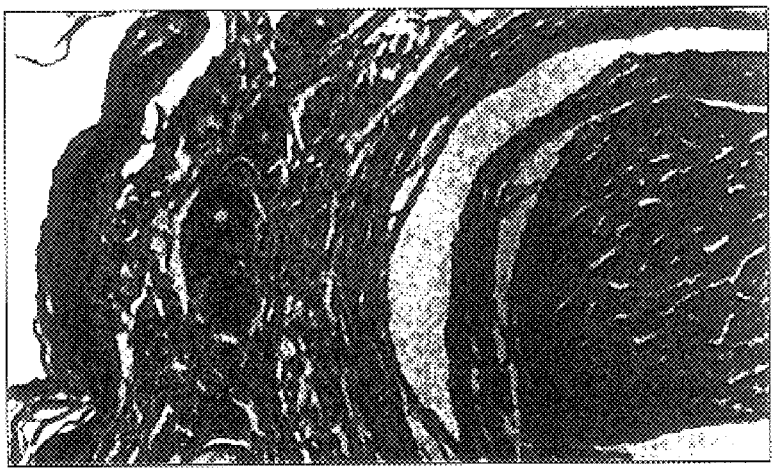
FIG. 18 depicts a representative histology of the paw (a) control; (b) arthritic; (c) $INH_2BP$ treatment+arthritis. Note the reduction in the degree of mononuclear cell infiltration in the paws of the $INH_2BP$-treated arthritic animals. Magnification is ×20.
Figure 18B:
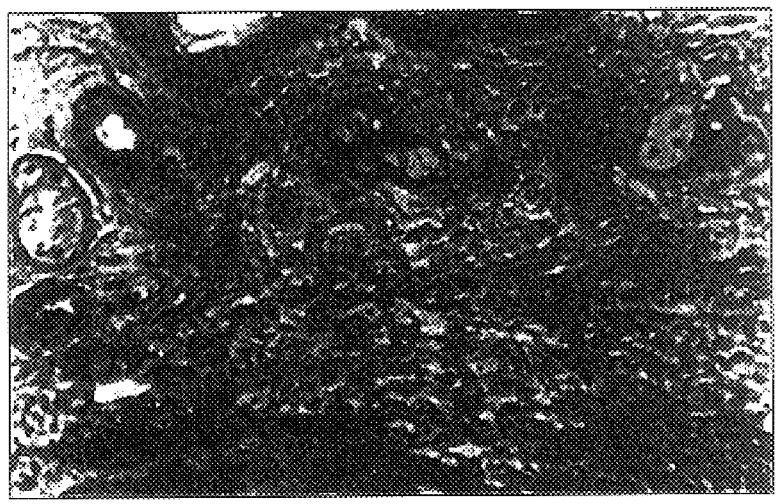
Figure 18C:
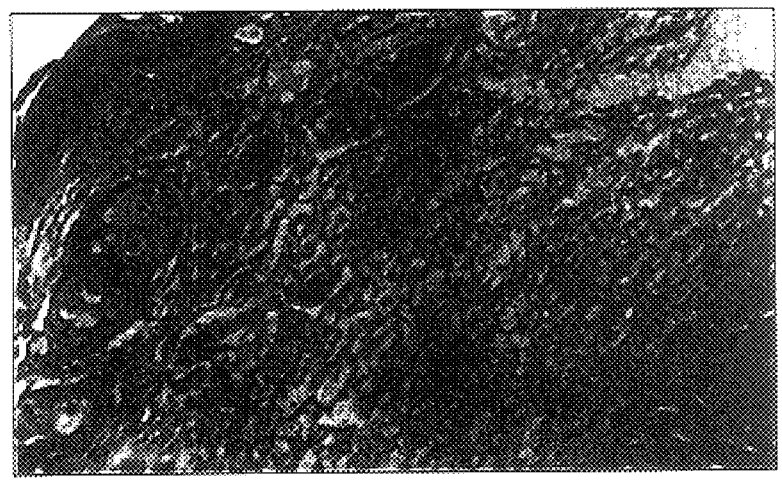

Based on our in vitro data indicating the importance of the peroxynitrite-PARS pathway in cell injury, we used INH$_2$BP to define the role of PARS in a mouse model of collagen-induced arthritis. Between Days 26–35 after the first collagen immunization, animals progressively developed arthritis (FIG. 17a–b). INH$_2$BP reduced the incidence of arthritis until Day 33 and reduced the severity of the disease throughout the experimental period. At Day 35, histological evaluation of the paws in the vehicle-treated arthritic animals revealed signs of severe suppurative arthritis, with massive mixed (neutrophil, macrophage and lymphocyte) infiltration. In addition, severe or moderate necrosis, hyperplasia and sloughing of the synovium could be seen, together with the extension of the inflammation into the adjacent musculature with fibrosis and increased mucous production (FIG. 18b). In the INH$_2$BP treated animals, the degree of arthritis was significantly reduced: a moderate, primarily neutrophil infiltration into several of the larger joints, coupled with mild to moderate necrosis and hyperplasia of the synovium (FIG. 18c).

EXAMPLE 4

Here we demonstrate that inhibition of PARS with the novel, potent PARS inhibitor 5-iodo-6-amino-1,2- benzopyrone (INH$_2$BP) protects against peroxynitrite-induced cell death in C6 glioma cells in vitro, and protects against the development of infarct and neurological deficit in a murine stroke model.

Methods

In vitro studies

The rat astrocytoma cell line C6 was cultured in Ham's F12 medium with 15% horse serum and 2.5% fetal calf serum. After a 10 min INH$_2$BP (1–100 µM) or vehicle pretreatment, cells were stimulated with peroxynitrite (500 µM) for 20 min (PARS assay) or 1 h (MTT and LDH assay) at 37° C. The incorporation of tritiated NAD$^+$ into nuclear proteins, an index of PARS activation was measured, as described by Szabó et al., J. Clin. Invest. 100:723–735 (1997). Reduction of [3-(4,5-dimethylthiazol-2-yl)-2,5-diphenyltetrazolium bromide] (MTT), an indicator of mitochondrial respiration, was measured, and cell membrane injury was quantitatively assessed by the measurement of lactate dehydrogenase (LDH) release. Id.

In vivo studies.

Adult male 129/SV mice were anesthetized with halothane. A 2 hour ischemia, followed by a 22 hour reperfusion, was induced with a 8.0 nylon monofilament coated with silicone resin/hardener mixture as described by Hara et al., J. Cereb. Blood Flow Metab. 16: 605–611 (1996). INH$_2$BP 10 mg/kg or 30 mg/kg in 5% dimethylsulfoxide (DMSO) in phosphate buffered saline (PBS, pH 7.4) was administered in a volume of 0.3 mL i.p. 2 hours before induction of ischemia. Control animals were injected i.p. with a corresponding volume of 5% DMSO in PBS. Infarct measurements were performed in five coronal 2 mm-sections with an image analysis system (Huang et al., Science 265:1883–1885 (1994)). Neurological deficit was also assessed by a 1–4 scoring system by Hara et al., supra.

Data analysis.

Data are presented as mean ±standard error (SE). Comparisons were made by two-tailed student's t-test. For neurological deficits, Kruskal-Wallis One Way Analysis of Variance on Ranks followed by Dunn's test was used. P<0.05 was considered statistically significant.

Results

INH$_2$BP inhibits peroxynitrite-induced PARS activation and neuronal injury in glial cells in vitro.

Figure 19A:
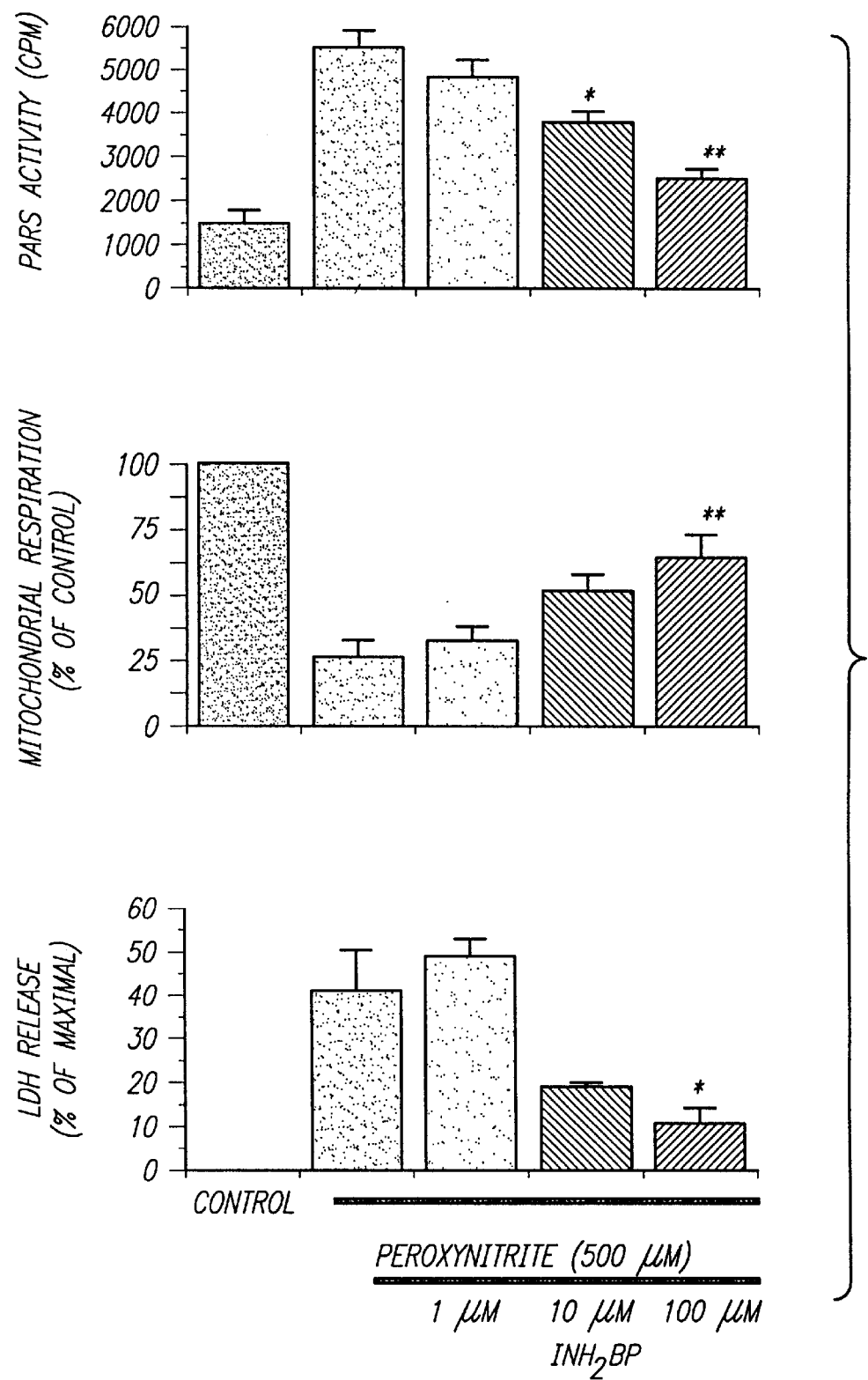
FIG. 19 represents (A) $INH_2BP$ prevention of PARS activation (top panel), the decrease in mitochondrial respiration, (middle panel) and LDH release (bottom panel) in peroxynitrite (500 $\mu M$) stimulated C6 cells. (B) Reduction in infarct size by $INH_2BP$ in stroke. Brain infarct volume (top panel) and brain infarct area (bottom panel) in vehicle-injected mice (diamonds) and mice treated with 10 or 30 mg $kg^{-1}$ $INH_2BP$ is presented. Data are presented as mean ±SE (n=6–12 and 8–11 per group in panels a and b, respectively) *p<0.05 or **p<0.01 vs vehicle.

Pretreatment with INH$_2$BP (1–100 µM) caused a dose-dependent inhibition of the peroxynitrite induced activation of PARS in the C6 cells. The most potent effect of INH$_2$BP was achieved with 100 µM concentration (FIG. 19a). Peroxynitrite induced a decrease in MTT reduction and an increase in the LDH levels in the culture medium, indicative of suppressed mitochondrial respiration and disrupted cell membrane integrity, respectively (FIG. 19a). INH$_2$BP dose-dependently protected against peroxynitrite-induced injury (FIG. 19a).

INH$_2$BP reduces infarct size after transient middle cerebral artery occlusion.

Figure 19B:
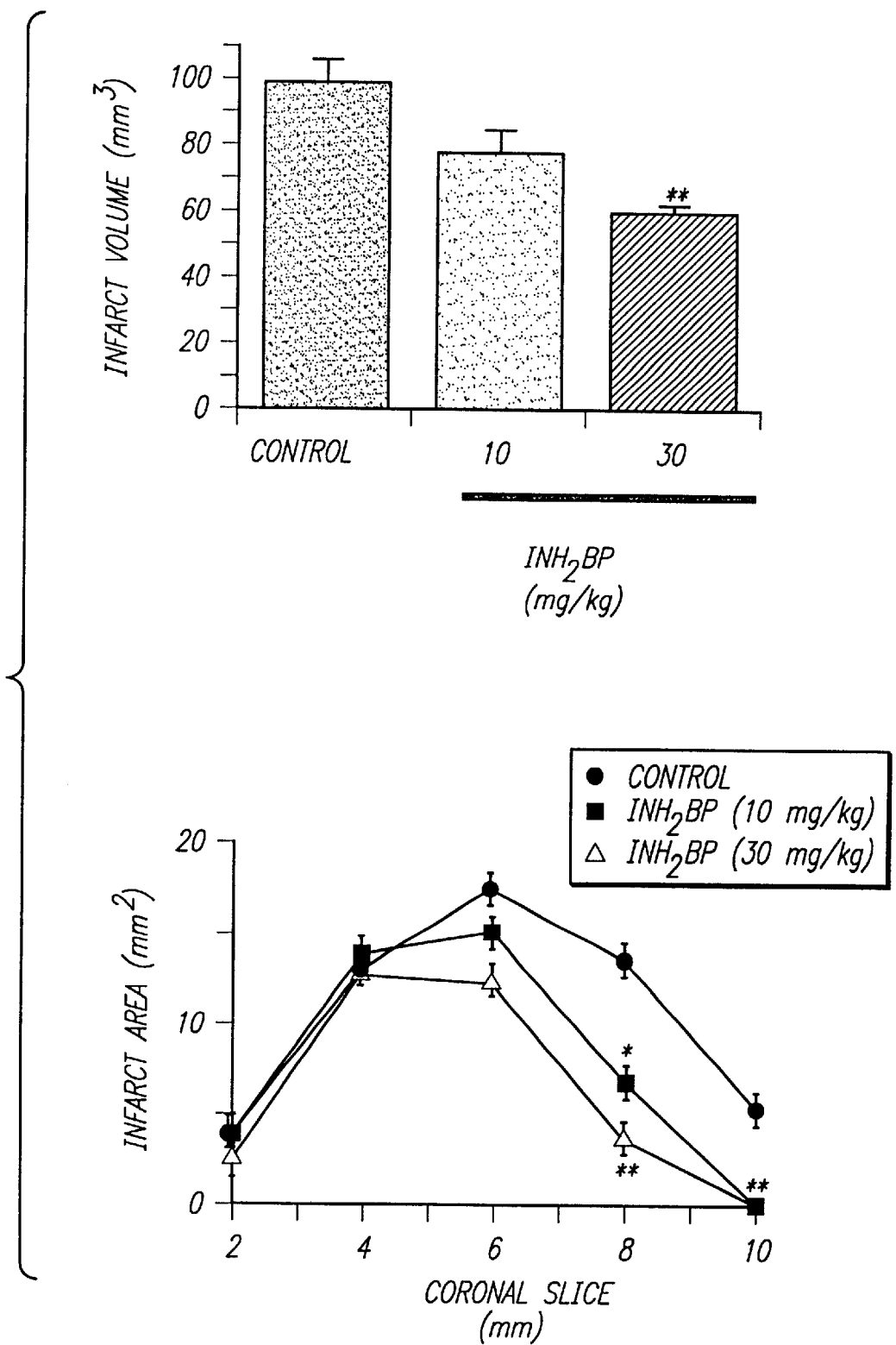

Pretreatment with 30 mg/kg i.p. (n=8) 2 hours before ischemia significantly reduced infarct size after 2 hours of middle cerebral artery occlusion and reperfusion in 129/SV mice compared to controls (n=10) (FIG. 19b). With INH$_2$BP at 10 mg/kg (n=11), there was a trend to smaller infarct sizes compared to controls (FIG. 19b). All animals exhibited a neurological score of 2 or higher 30 minutes after the onset of ischemia. At 22 hours reperfusion, deficits were significantly (p<0.05) improved in the 30 mg/kg group compared with controls (1.8±0.1 vs 1.2±0.3 vs 1.0±0.2 in vehicle-treated, 10 and 30 mg/kg INH$_2$BP-treated animals, respectively).

Discussion

These data demonstrate that inhibition of PARS with INH$_2$BP provides a dose-dependent protection against glial cell injury in vitro and against stroke development in vivo. Along with a reduction in infarct size, neurological deficit was improved in treated animals, indicating functional recovery after PARS inhibition.

A significant portion of the neuronal injury is related to overproduction of NO, due to the N-methyl-D-aspartate receptor activation, and subsequent activation of the neuronal NO synthase in the reperfused brain. NO combines with superoxide, peroxynitrite, in turn, induces rapid and pronounced oxidative and peroxidative injury (Dalkara et al., Int. Rev. Neurobiol. 40: 319–336 (1997)). Part of this injury is related to DNA single strand breakage and activation of an energy-consuming cycle by PARS. The data provided herein demonstrate that the experimental therapy of stroke may represent a novel indication for the development of INH$_2$BP and related PARS inhibitors.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

What is claimed is:

1. A method for treating arthritis in an animal or mammal, said method comprising the step of administering to an animal or mammal a therapeutically effective amount of an pADPRT inhibitory compound, wherein said pADPRT inhibitory compound is not a benzamide.

2. The method of claim 1 wherein the compound is selected from the group consisting of:

a compound having the structural formula:

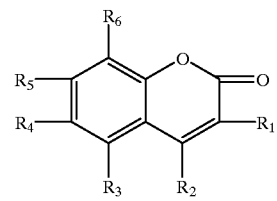

(I)

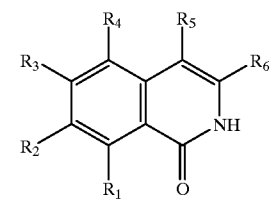

(II)

wherein $R_1$, $R_2$, $R_3$, $R_4$, $R_5$ and $R_6$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are always hydrogen and at least one of the six $R_1$, $R_2$, $R_3$, $R_4$, $R_5$ and $R_6$ substituents are selected from the group consisting of amino, nitroso and nitro.

* * * * *